US012201554B2

(12) United States Patent
Orr et al.

(10) Patent No.: US 12,201,554 B2
(45) Date of Patent: Jan. 21, 2025

(54) EQUINE CRYOTHERAPY DUAL COMPARTMENT BOOT

(71) Applicants: Susan B. Orr, Jacksonville Beach, FL (US); Joan C. Gariboldi, Lexington, KY (US)

(72) Inventors: Susan B. Orr, Jacksonville Beach, FL (US); Joan C. Gariboldi, Lexington, KY (US)

(*) Notice: Subject to any disclaimer, the term of this patent is extended or adjusted under 35 U.S.C. 154(b) by 927 days.

(21) Appl. No.: 17/205,662

(22) Filed: Mar. 18, 2021

(65) Prior Publication Data

US 2021/0275350 A1 Sep. 9, 2021

Related U.S. Application Data

(63) Continuation-in-part of application No. 16/786,192, filed on Feb. 10, 2020, now Pat. No. 11,701,210, which is a continuation-in-part of application No. 15/626,081, filed on Jun. 17, 2017, now abandoned.

(60) Provisional application No. 62/351,955, filed on Jun. 18, 2016.

(51) Int. Cl.
*A61F 7/10* (2006.01)
*A01K 13/00* (2006.01)
*A61F 7/00* (2006.01)

(52) U.S. Cl.
CPC ............ *A61F 7/103* (2013.01); *A01K 13/007* (2013.01); *A61F 2007/0043* (2013.01); *A61F 2007/0045* (2013.01); *A61F 2007/105* (2013.01)

(58) Field of Classification Search
CPC .............. A61F 7/103; A61F 2007/0043; A61F 2007/105; A01K 13/007
See application file for complete search history.

(56) References Cited

U.S. PATENT DOCUMENTS

| | | |
|---|---|---|
| 3,905,367 A | 9/1975 | Dapcich |
| 5,152,285 A | 10/1992 | Gnegy |
| 6,086,609 A | 7/2000 | Buckley |
| 8,166,734 B2 | 5/2012 | Ruetenik |
| 9,498,638 B2 | 11/2016 | Ruetenik |
| 2002/0074136 A1 | 6/2002 | Wiltz |
| 2010/0095641 A1 | 4/2010 | Ruetenik |
| 2010/0132226 A1* | 6/2010 | Dochter ............. A43B 23/0295 36/136 |
| 2011/0271652 A1 | 11/2011 | Wollowick |
| 2012/0083725 A1 | 4/2012 | Mattes |
| 2012/0330376 A1 | 12/2012 | Flynn et al. |
| 2014/0209594 A1 | 7/2014 | Besner |
| 2015/0119772 A1 | 4/2015 | Ruetenik |

(Continued)

FOREIGN PATENT DOCUMENTS

WO 2015120368 A3 11/2015

*Primary Examiner* — Kaitlyn E Smith
(74) *Attorney, Agent, or Firm* — Trace H. Jackson; Rogers Towers, P.A.

(57) ABSTRACT

An equine cryotherapy overleg device that encircles the lower limb of a subject horse and provides cryotherapy to the subject horse. The one-piece device includes upper and lower fasteners, a pastern area that will hold ice and ice water and a vertical zipper. The arrangement of the hoof cover, and hoof slipper allow for free movement of the subject horse and for a thermal fluid to contain ice and prevent the ice from migrating under the subject horse hoof.

19 Claims, 23 Drawing Sheets

(56) References Cited

U.S. PATENT DOCUMENTS

| | | | |
|---|---|---|---|
| 2015/0156989 A1* | 6/2015 | Ruetenik | A01K 13/007 168/28 |
| 2015/0157435 A1 | 6/2015 | Chasins et al. | |
| 2016/0100802 A1 | 4/2016 | Newman | |
| 2016/0354232 A1 | 12/2016 | Rozental | |

* cited by examiner

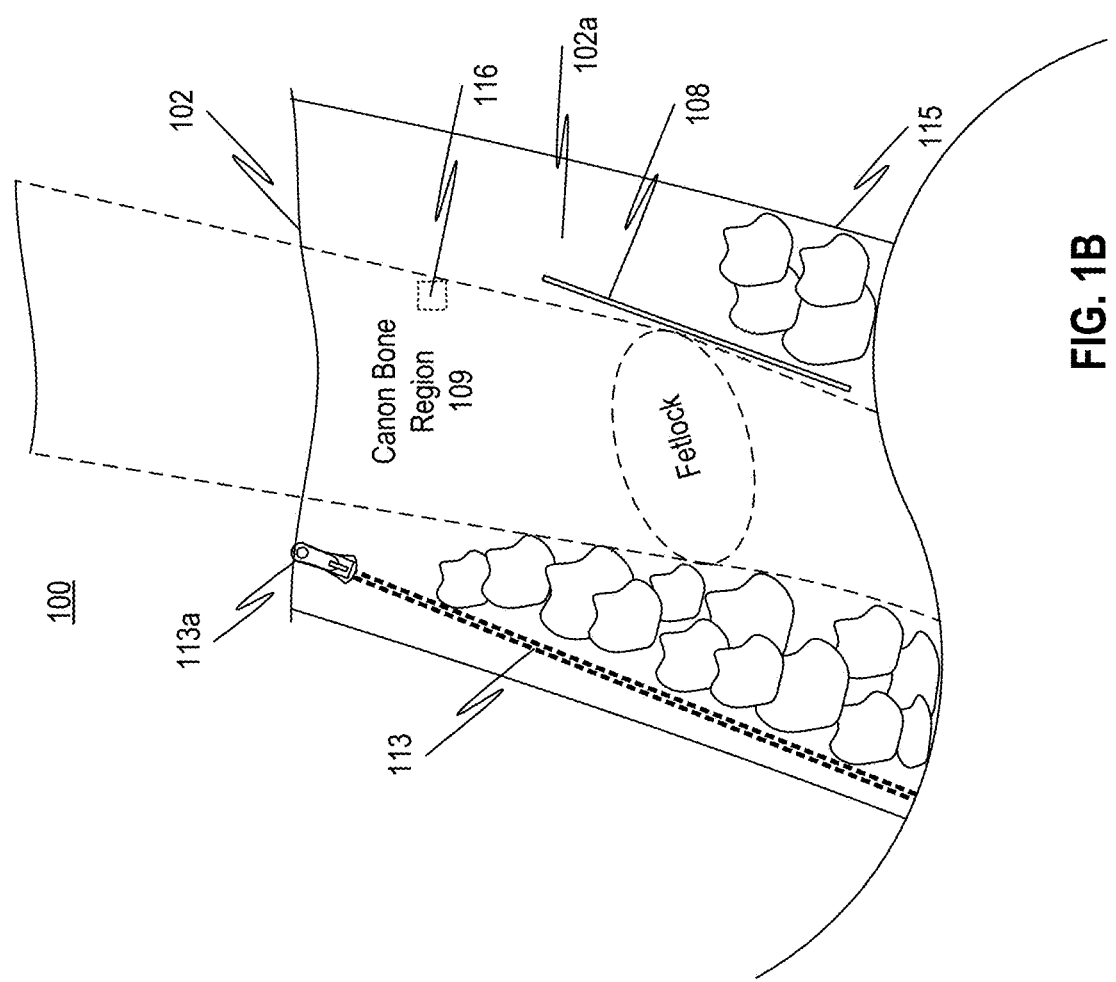

900

| With the cryotherapy boot in an inside out hoof cover device in an unfastened state, placing the hoof cover bottom against a bottom of a hoof of a patient horse |
|---|
| 901 |

| With the cryotherapy boot in an inside outstate state and the hoof cover device in an unfastened state, and the hoof cover bottom against the hoof of the patient horse, pulling the hoof cover over the hoof of the patient horse |
|---|
| 902 |

| Fasten the hoof cover fastening device to hold the hoof cover in a state snugly positioned around the hoof |
|---|
| 903 |

| With the hoof cover fastening device in a fastened state and the hoof cover positioned snugly about the hoof of the patient horse |
|---|
| 904 |

| The upper shell in an open state with the upper compartment access device in an unfastened state, fastening the upper compartment tether thereby causing an outer shell to be supported in an upright position on a patient horse's leg |
|---|
| 905 |

| With the hoof in the cryotherapy boot and secured by in the lower shell by the hoof cover, and the upper compartment tether secured around the patient horse's leg thereby supporting the outer shell in a vertical position on the leg of the patient horse, inserting ice into an ice containment area within the upper shell |
|---|
| 906 |

| Raise an upper containment access device to cause the upper shell to form a contiguous perimeter around the leg of the patient horse. |
|---|
| 907 |

FIG. 9

EQUINE CRYOTHERAPY DUAL COMPARTMENT BOOT

CROSS-REFERENCE TO RELATED APPLICATIONS

This application claims the benefit of U.S. patent application Ser. No. 16/786,192, filed on Feb. 10, 2020, entitled EQUINE CRYOTHERAPY OVERLEG DEVICE, which is a continuation in part of U.S. patent application Ser. No. 15/626,081, filed on Jun. 17, 2017, entitled EQUINE CRYOTHERAPY BOOT 100, which claims priority to U.S. Provisional Patent Application Ser. No. 62/351,955, filed on Jun. 18, 2016, entitled EQUINE CRYOTHERAPY BOOT 100, which the entire content of all are hereby incorporated by reference in its entirety.

FIELD OF THE DISCLOSURE

The present disclosure relates to apparatus and methods to effectively provide cryotherapy to hoof and lower limb of an equine animal such as a horse, a mule, a donkey, a burro, a zebra, and so forth (generically, "horse"). More specifically, the present invention provides for a safe overleg device that allows a subject horse to move about a stall freely and comfortably, while its hoof is receiving a requisite amount of cryotherapy.

BACKGROUND OF THE DISCLOSURE

Ice wraps around a horse limb and hoof have been known to provide relief of symptoms related to inflammation of the tissue experienced by the horse. More importantly, the application of ice to a horse's foot or hoof has been shown to prevent a serious and potentially fatal condition of laminitis. However, current methods to ice a horse's feet require that the horse be restrained or be minimally mobile during therapy, which may last hours each day for many days. Previous designs of wraps to provide ice and/or cold water to a horse's feet have not provided sufficient support for the therapy device, or insufficient cooling of the hooves, and have allowed ice to migrate under a horse's foot. Current devices will dislodge the therapy device and disrupt the therapy if the horse is left to move freely around its stall.

Cryotherapy, or an ice therapy of a horse's hoof, is effective in the prevention of the often-fatal condition of laminitis. Endotoxemia, which is associated with septic shock leads to the activation of several enzymatic reactions that results in severe inflammation and the development of laminitis. Laminitis is a debilitating, if not fatal condition, where there is a loss of the integrity of the attachment of the hoof capsule to the bone in the horse's hoof.

Currently, an effective and efficient method to provide topical ice therapy continuously to a horse's foot, which allows the animal to be freely mobile in a stall, does not exist. Most equine hospital staff provide topical ice therapy to a distal limb of a horse by placing the horse's foot in a used, empty five-liter intravenous fluid bag, filling the intravenous bag with ice, then taping it to the horse's fetlock with duct tape. This methodology is cumbersome, time consuming and can create sores on the horse's skin. Additionally, this method allows the ice to migrate under the horse's foot, creating discomfort and potentially more inflammation.

Cold therapy boots have been developed, but the currently available cold therapy boots which allow a horse to be mobile, only facilitate the placement of cold packs over the hoof capsule and do not provide effective cooling to the lower limb of the horse. Several forms of large ice therapy boots and baths exist that effectively cool the foot and lower limb of the horse, but these products can only be used while the horse is immobilized. Accordingly, a need exists for a device to facilitate cryotherapy for a horse, while preventing ice from migrating under the foot, and also allowing the horse to move comfortably and freely in a stall.

SUMMARY OF THE INVENTION

Accordingly, the present invention provides a thermal containment device that may be generally described as an equine cryotherapy overleg device. The overleg device comfortably and safely provides topical cryotherapy to a horse's hoof and distal limb. Topical therapy typically will include ice, chilled fluid, such as ice water, or ice salt water. The equine cryotherapy overleg device allows a horse receiving treatment to move freely without a need for being immobilized. The dual compartment design facilitates easy, efficient, and effective placement of ice around horse's the lower limb, below the knee and hock and prevents ice from becoming lodged beneath the horse's hoof.

The present invention teaches a one-piece cryotherapy overleg device that includes two compartments and two separate fastening devices that secure the overleg device, safely and effectively, to a) the horse's hoof; and b) the horse's cannon bone.

A first (lower) compartment envelopes the horse's hoof and is secured with a first fastening device that is generally referred to herein as a lower fastening device or hoof slipper. The lower fastening device employs a stretchable material (such as, for example neoprene or other synthetic rubber produced by polymerization of chloroprene). The lower fastening device is configurable to encircle a horse's hoof and be removably secure the first compartment with a fastener such as a hook and loop fastener (such as, for example a Velcro™ fastener system). This lower fastening device not only secures and holds the first compartment of the overleg device in place; it also prevents the migration of ice under the horse's hoof.

A second fastening device, referred to herein as the tether or upper fastening device, is also constructed from a stretchable material, such as neoprene and encircles the cannon bone between the carpus or tarsus and fetlock. The upper fastening device is also removably secured with a fastening device, such as hook and loop material (e.g., Velcro®), snaps, a strap and buckle, strap and button or other device, and functions to safely and effectively maintain the overleg device on the limb while the overleg device contains ice. The upper fastening device safely distributes pressure over the cannon bone of the patient horse, allowing the horse to be mobile, while not affecting blood flow to the horse's lower limb. The overleg device is operative to contain ice and cold water in the second (upper) compartment which acts as a containing area (and may sometimes be referred to as a fluid containment area or ice containment area). The upper compartment is supported by securing the tether around a portion of the equine leg from the tarsus or carpus to the fetlock. The tether is fixedly attached to a material forming the upper compartment thereby providing support to the upper compartment. The material forming the upper compartment may be referred to as the upper shell. The upper compartment is formed to encompass the equine leg and attaches to the hoof cover, which may in some embodiments contain a hoof slipper.

The zipper or other fastening device is longitudinally placed along a forward surface of the overleg device which facilitates the quick and easy addition of ice to the boot 100 and also maintains a chilled solution around a treated area.

As the ice in the boot 100 melts, it can be replaced, as frequently as required, when it melts. The thermal control fluid (water, in some embodiments) may be allowed to seep from the containment area when it rises to the level of the longitudinal zipper.

BRIEF DESCRIPTION OF THE DRAWINGS

The accompanying drawings, that are incorporated in and constitute a part of this specification, illustrate several embodiments of the disclosure and, together with the description, explain the principles of the disclosure:

FIG. 9 illustrate method steps that may be executed in some embodiments of the present invention.

DETAILED DESCRIPTION

The present invention provides for the methods and apparatus for application of ice to a lower limb and hoof of a horse to effectively and efficiently cools the limb and/or hoof while allowing the horse to move freely about in a stall or other localized area. The apparatus generally includes dual compartments formed of stretchable material and positioned around a hoof and a lower leg of a horse. Also included are two interior fastening devices, each fastening device associated with a respective compartment and acting in concert to properly attach the boot to the equine hoof and lower leg in a manner conducive to the patient horse being free to move about a stall. The boot is formable in a general shape such that one compartment closes matches a size and shape of the hoof and a second compartment includes a tether that is fastenable about the leg of the horse and able to contain ice thermal proximity to the leg and hoof of the horse.

Access to the second compartment is provided via a longitudinal zipper in order to place ice in the second compartment. Cold water (sometimes referred to as a "thermal control fluid") is leached from the second compartment via weeping through the zipper or via a weeping portal included in a shell defining the second compartment.

The lower compartment encompasses the horse's hoof and may also be formed with a stretchable material, The lower compartment forms a hoof cover positioned around the horse's hoof and covering at least a portion of the hoof.

A hoof slipper may be included on the bottom of the hoof cover to provide a suitable surface for the horse to walk on and be rugged enough to withstand the weight and movement of the horse.

Methods include a process for effectively and efficiently placing the dual compartment boot on a patient horse without causing the horse stress and for securing the boot around a horse's leg and hoof before providing ice into the containing area. Methods also include processes for: a) easily placing ice into the boot; b) removing water from the containment area that results from ice placed within the containment area melting; and c) preventing ice from migrating below the equine hoof in a fashion that would allow the horse to step on the ice.

Figure 1:
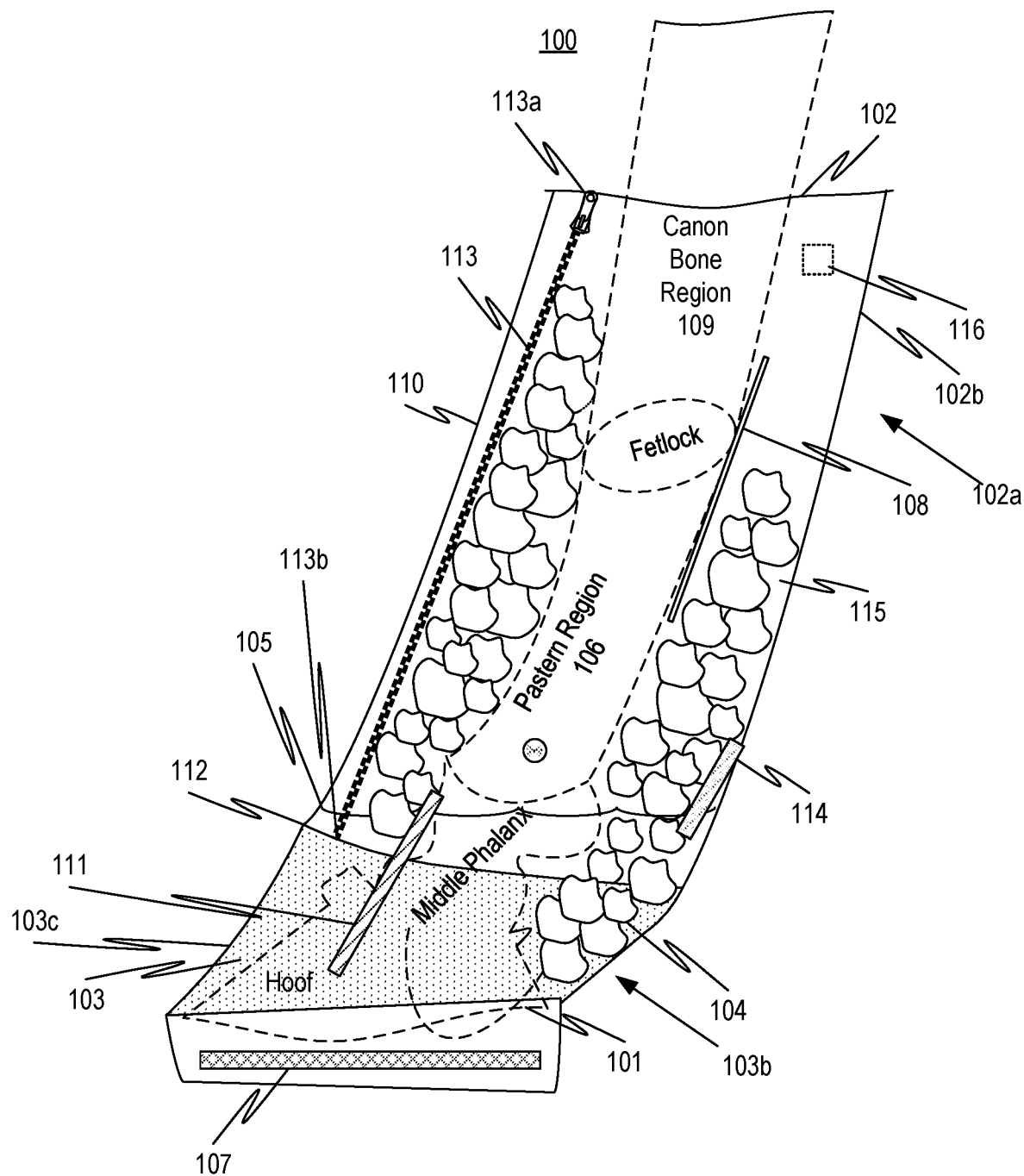
FIG. 1 illustrates an equine cryotherapy overleg device according to some embodiments of the present invention.
Figure 1A:
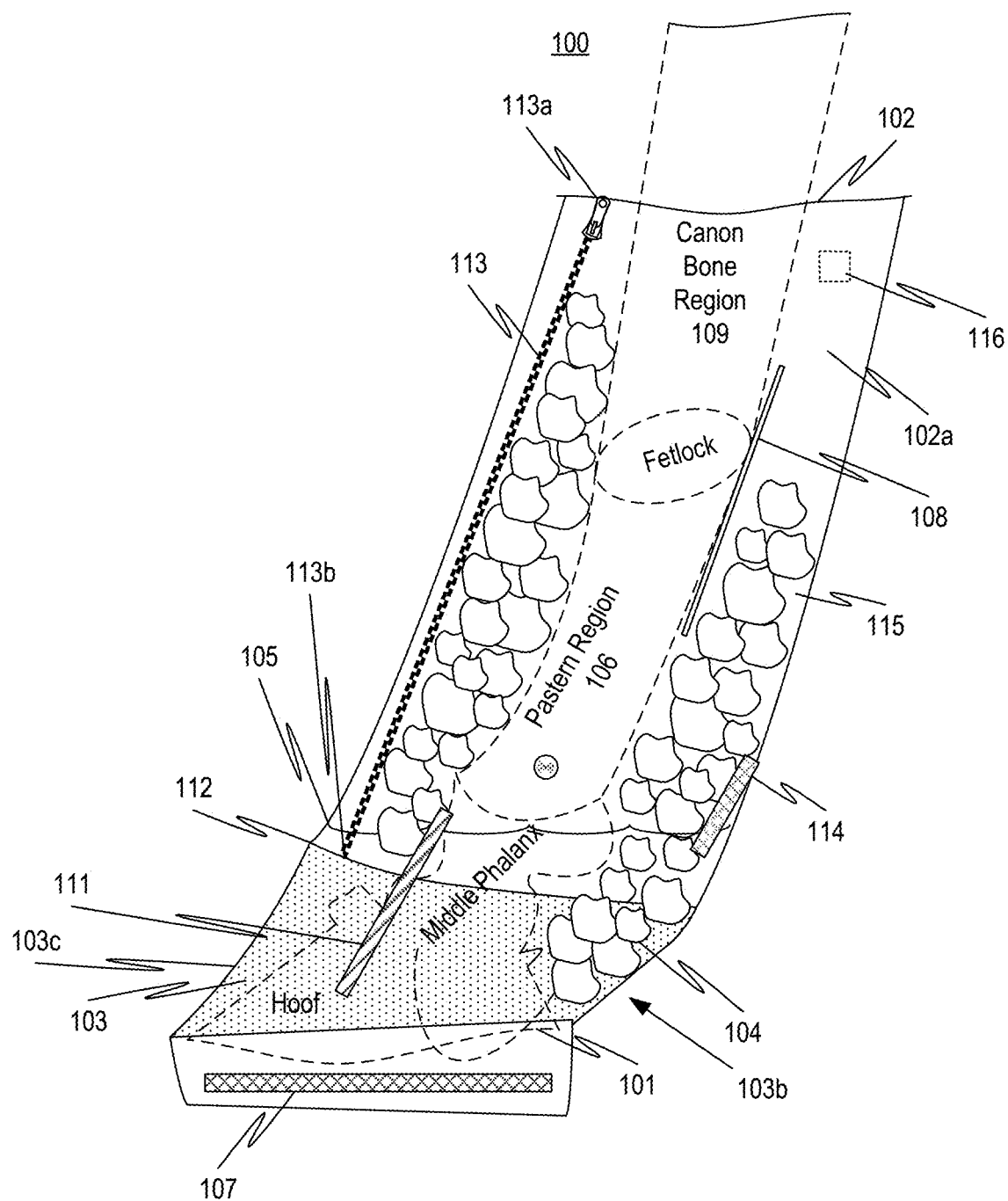
Figure 1C:
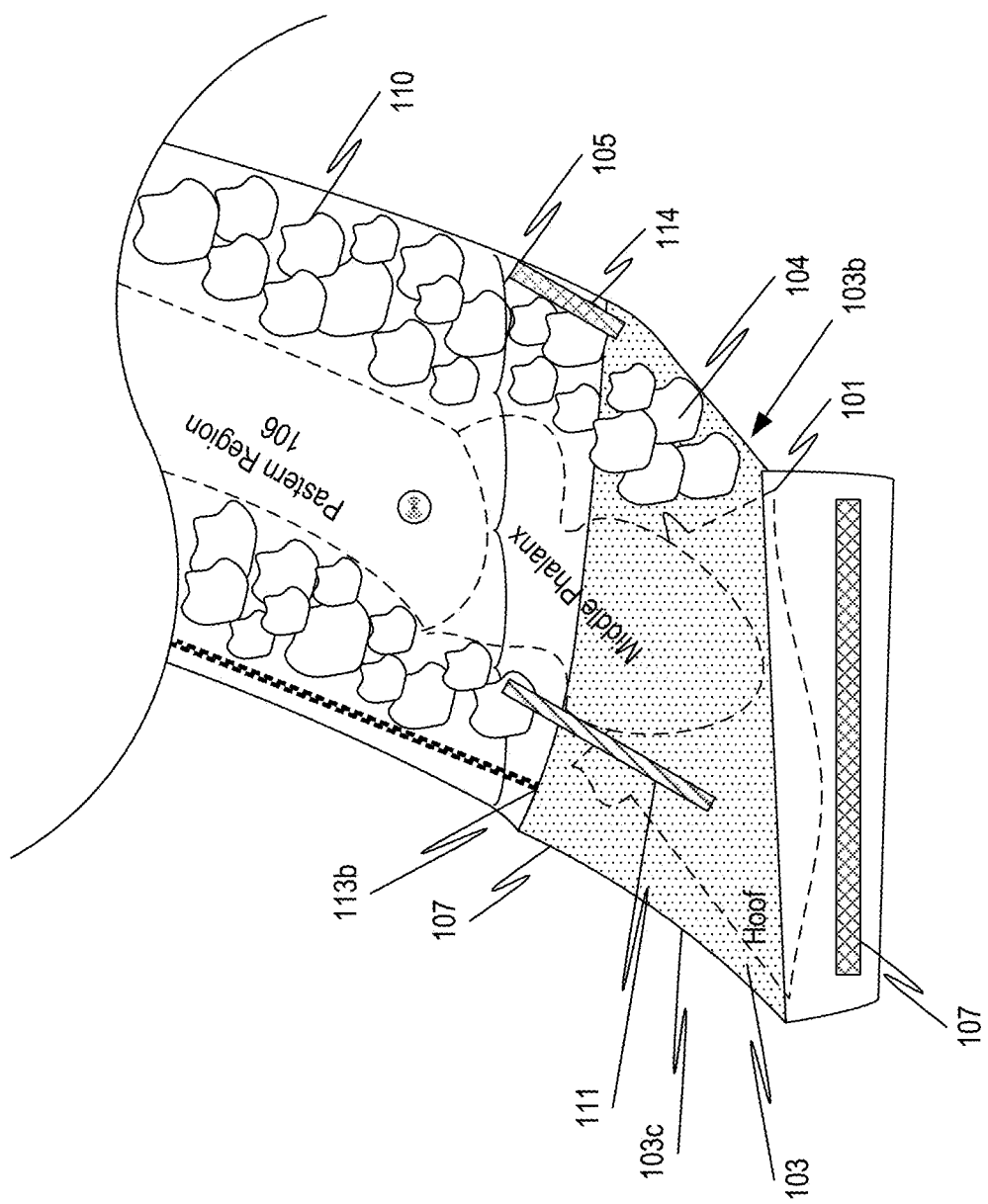

Referring now to FIG. 1, a cryotherapy boot 100 according to the present invention, comfortably and safely provides topical cryotherapy and covers an area of a horse's hoof and distal limb from the bottom of the foot or hoof 101 to a bottom of the carpus or tarsus 102. The cryotherapy boot 100 fits over a hoof of a horse being treated and holds ice 104 and allows thermal control fluid 105 (e.g., chilled fluid resulting from melting ice) to weep from an ice containment area. In some embodiments, a thermal agent other than ice may be contained within the ice containment area 115, for example, a thermal gel material, or chilled pack, or a thermal electric device may be placed in the ice containment area. The ice containment area is preferably located around a pastern region 106 and down to the sole of a horse's hoof 101.

The equine cryotherapy boot 100 adheres to a size and shape that allows a horse receiving treatment to move in a stall or in other confined area without being tied in position or otherwise constrained to a particular position. Methods of placing the boot 100 on a horse facilitate easy and effective placement of a thermally beneficial substance, such as ice, in thermal proximity to an area of the horse's leg to be treated.

A first compartment, which may be referred to herein as the upper compartment 102a is contained within an upper shell 102b of the boot 100. The upper shell 102b is preferably fashioned from a yielding material, such as a compliant synthetic rubber or other product derived from polymerization of chloroprene. Specific upper shell 102b materials may include, for example: neoprene, poly-paraphenylene terephthalamide fiber, or a carbon fiber, such as Superfabric®. The upper shell 102b may be positioned around the canon bone region 109 and the pastern region 106 and extend to a hoof cover 103 that encompassed a hoof 101 of the patient horse. As described in more detail below, a longitudinal zipper 113, or other upper compartment access device, may be opened to allow access to the upper compartment 102a. Access to the upper compartment 102a may be facilitate, for example the placement of ice 104 within the upper compartment, and/or the fastening and unfastening of an upper compartment tether 108.

The upper compartment tether 108 may be fixedly attached to the upper shell 102b via a stitched seam or other attachment means, including for example, rivets, buttons, snaps or other fasteners. In some embodiments, the upper compartment tether 108 may be removably attached to the upper shell 102b, such as via a hook and loop interface, although a more permanent attachment, such as a sewn in seam is preferable.

A zipper 113 extends from an open end 113a that is preferably located at an upper shell edge 110 to closed end 113b located at a lower portion of the boot 100. A low point of the closed end 113b will create a high point for contained thermal control fluid 105 if the zipper 113 acts as the lowest weeping means for the thermal control fluid 105 to exit the ice containment area 115.

According to the present invention, ice 104 is placed in the upper compartment 102*a*. The ice 104 is subjected to body heat of the horse and ambient temperature of a stall causing the ice 104 to melt which introduces water (or other thermal control fluid 105 if the ice is not pure H2O). Inherent interstices of the zipper 113 allow water resulting from melting ice to permeate the zipper 113 and weep out of the ice containment area 115. Some embodiments may include a weep portal 114 that contains ice within the upper compartment, but allows water to weep through and escape from the boot 100.

The cryotherapy boot 100 includes a lower compartment 103*b* generally defined by an interior of a lower shell 103*c* when the boot is turned right side out. The lower compartment encompasses a hoof cover 103 when the boot 100 is in a right side out state. Accordingly, the lower compartment 103*b* will encompass the hoof cover 103 when the cryotherapy boot 100 is installed on a horse. The hoof cover 103 secures the lower portion of the boot 100 to the hoof 101 and ensures that ice 104 will not migrate under the horse's hoof 101.

A lower shell 103*c* is connected to the upper shell 102*b*. In preferred embodiments, the lower shell 103*c* is connected to the upper shell 102*b* via a generally lateral hoof cover seam 112 that may be stitched, glued, riveted, or fastened by other means that secures the hoof cover 103 with a hoof cover seam 112 around a circumference of the upper shell 102*b*. The hoof cover seam 112 is preferably positioned around a top of the hoof 101 or a bottom of the pastern region 106 of the horse. The hoof cover seam 112 may include a "hoof shaped" circumference of approximately 12 inches for a small boot 100, to approximately 20 inches for a large equine boot 100.

The hoof cover 103 is fashioned from a rugged material, such as Superfabric®, a poly-paraphenylene terephthalamide fiber, carbon fiber, or a compliant synthetic rubber or similar product derived from polymerization of chloroprene. The hoof cover 103 will preferably be capable of resisting scuffs as a subject horse moves about and may strike the hoof cover 103 against concrete, asphalt or a similar hard surface. The hoof cover 103 is formed in shape to closely mimic a hoof 101.

In some embodiments, a hoof slipper 107 may be included within the hoof cover 103. The hoof slipper 107 forms a durable bottom portion of the hoof cover 103. The hoof slipper 107 is preferably capable of resisting deterioration from a horseshoe while supporting the subject horse's weight. In some embodiments, a hoof slipper 107 may provide a cushioning effect to the horse's foot while the horse is standing or walking. In addition, a hoof slipper 107 may include a contour designed to support specific areas of the hoof, such as for example a perimeter area (similar to a horseshoe shape), or in some embodiments a central area (generally opposite of a horseshoe). Both the hoof cover 103 and the hoof slipper 107 may be formed in various matched sizes to accommodate different sized horse hooves, from young horses (foals) to large draft horses.

Some preferred embodiments include a hoof cover fastening device 111 (sometimes referred to as a lower fastener) that is accessible by opening the upper shell 102*b* and is preferably located within the upper shell 102*b* when the cryotherapy boot 100 is fully installed on a patient horse. The hoof fastening device 111 may be set in an unfastened position while placing the hoof cover 103 on a horse and in a fastened position to secure the hoof cover 103 to the hoof 101 of the horse and protect the horse from having ice migrate down below the horse's hoof 101. The hoof cover fastening device may be formed from a pliable, durable material with sufficient tensile strength to secure the hoof cover 103 to the hoof 101 while a horse moves about a stall. The Hoof cover fastening device 111 may include a removable attachment mechanism, such as, for example, hook-and-loop fastener, snaps, elastic straps, buckles and the like.

The hoof cover 103 is preferably pliable enough to allow it to be turned inside out for placement of the hoof cover 103 on the hoof 100. The hoof cover 103 is generally formed in the shape of a hoof 101, it is dependent on the hoof slipper 107 to maintain in proper position as the subject horse moves about. In preferred embodiments, a hoof cover 103 is enveloped in a lower shell 103*c* while the hoof cover 103 is installed on a horse.

The hoof cover 103 is preferably fixedly and removably attached to the hoof slipper 107. The hoof cover 103 affixes the lower portion of the boot 100 securely over the hoof 101 capsule and will cover the majority of the hoof 101. The hoof cover 103 is generally formed in a shape to mimic a shape of a hoof 101 capsule. Some hoof covers 103 and/or hoof slippers 107 may be formed specific to a subject horse via custom manufacture. Additionally, a hoof cover 103 and/or hoof slipper 107 may be formed with various sizes, to accommodate a particular breed, size or age of a subject horse. By way of non-limiting example, a hoof slipper 107 may include a thicker bottom or sole, to provide more lift or padding or slope to the actual angle of the horse's foot. Other hoof slippers may provide increased support to a central portion of a hoof 101 in a reverse pressure pattern of a traditional horseshoe in order to facilitate relief of laminitis. When fastened, the lower fastener 111 will secure the hoof cover 103 in place around the hoof 101 such that the hoof cover 103 prevents ice from migrating below the horse's hoof 101.

An upper compartment tether 108 (sometimes referred to as an upper fastener) is attached to an inner side of the upper or cannon pastern region 106 and is placed around the cannon bone region 109 of the horse being treated. The amount of tension holding the upper fastener to the horse's leg ensures that upper portion of the boot 100 will safely and effectively hold the pastern component up on the horse's leg and stop the boot 100 from drooping or moving laterally while filled with ice 104 and thermal control fluid 105. Proper tension and a flexible nature of the upper fastener prevents adversely affecting a subject horse's limb and blood circulation due to too much constriction. Proper tension will also be sufficient to maintain a position of the boot 100 as are forces introduced by the horse walking or otherwise moving its leg.

A height of the upper compartment 102*a* may vary or be selectable, for example within a range of about 12-20 inches. Preferably, the height will maintain ice 104 or other thermal control substance or fluid 105, or a combination thereof, around a pastern region 106 of a subject horse.

The provides for the thermal control fluid 105 to weep through a zipper (or other upper compartment access device) 113 or potentially through a dedicated weep portal 114. The zipper 113 and/or weep portal 114 may permit controlled passage of thermal control fluid 105 from the fluid containment area 115 to an area external of the boot 100. Since melted ice forms water that is by definition warmer than the ice 104, if too much water accumulates within the ice containment area 115, the remaining ice 104 will not be sufficient to adequately cool the horse's leg and/or hoof.

Therefore, the present invention provides for mechanisms (the zipper 113 and weep portal 114) for weeping the water away from the ice containment area 115.

Still further embodiments may include a sensor 116, such as a thermometer, thermistor or other indicator of thermal energy, to provide feedback on a condition within the boot 100. In some embodiments, the sensor 116 may include a wireless transceiver to allow it to transmit its readings to a receiving device. The receiving device may include a smart phone, wearable, or other suitable technology. The sensor 116 may transmit along any suitable modality that would not endanger the horse. These modalities may include Bluetooth® or Wi-Fi®.

Figure 2:
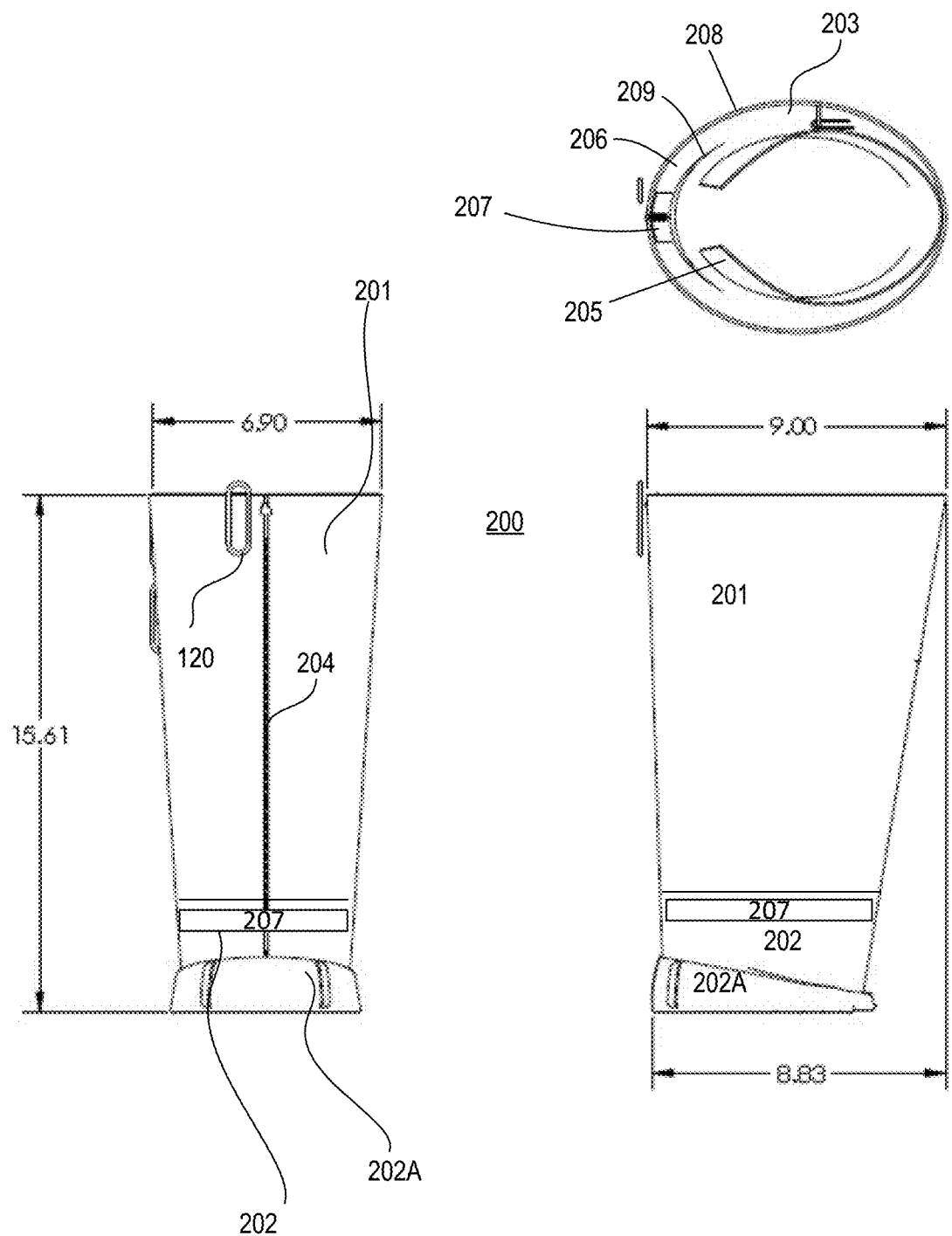
FIG. 2 illustrates an exemplary side view of an equine cryotherapy overleg device with chilled fluid contained within the boot 100.

Referring now to FIG. 2, aspects of some embodiments of a thermal overleg device 200 are shown. An upper portion 201 of the overleg device 200 may include an inner surface 209 attached to a tether 204 that may be fastened to secure the device 200 to the horse leg from the carpus (knee) or tarsus (hock) to the fetlock (ankle) via, for example, elastic or hook-and-loop fastener straps and so forth. The neoprene, or other water-holding or temperature-retentive material forming an outer portion 208 of the equine cryotherapy overleg device 200, may be sewn or otherwise fixedly attached to the upper securing device 205 of the equine cryotherapy overleg device 200. In preferred embodiments, the upper securing device 205 will safely secure the upper portion of the overleg device 200 to the horse's cannon bone region without disrupting blood circulation to the horse's lower limb and hoof. This singular device will contain and ice, and potentially a cytotherapeutic fluid to maintain provide a safe and effective method to cool a horse's lower limb, including the hoof. Additionally, some embodiments may include an additive to the thermally controlled fluid to keep the fluid generally microbe free and/or to provide better thermal stability.

The lower portion 201 of the overleg device 200 may also include a flexible lower securing device 207 that will securely fasten the lower portion to the hoor. The lower securing device 207 may include, for example, one or both of: an elastic strap and a hook-and-loop fastener strap.

The upper portion 201 includes a containment area 115 for ice and/or fluid. The containment area 115 may be fashioned from a durable, fluid-holding material. The outer portion material 203 of the upper portion 201 of the boot 100 may be sewn or otherwise fixedly attached to the upper fastener 112. The outer portion 203 contains the fluid containment area 115.

In some embodiments, the longitudinal zipper 113 can be unzipped to rapidly facilitate the addition of ice 104 to the boot 100. The zipper 113 also allows water to leak externally from the boot 100.

In some embodiments, the overleg device 200 may be filled with one of various thermal control fluids 105, such as fresh water, salt water, an alcohol, glycol (i.e., antifreeze), an oil, or various mixtures or solutions thereof. The fluid may be selected based on a desirable characteristic, such as a lower melting point, a higher rate of heat transfer, heat retention, viscosity, animal safety in case of leaks, corrosiveness, inertness, stability, and so forth.

In some embodiments, the upper fastening device 112 of the boot 100 is wrapped tightly enough around the canon bone region 109 so that the boot 100 substantially does not move, slip, slide, etc. when filled with ice 104 and thermal control fluids 105 and the horse is ambulatory. The boot 100 further includes an outer portion material 203 that is impermeable to unintended leakage of fluid, allowing fluid to leak from the exclusively from the weep portal 114 at the bottom of the zipper 113.

In some embodiments, a bottom of the boot 100 will have a lower fastening device to enclose the hoof and secure the lower portion of the boot 100 to the foot (hoof). In such embodiments, the very bottom of the boot 100 (and side edges near the bottom) may be constructed to be more puncture-resistant material, such as Superfabric®, than the top of the boot 100 to resist damage caused by the hoof as it bears the weight of the animal, or from sharp edges of the hoof, or from horseshoes nailed to the hoof, and so forth.

In some embodiments, a boot 100 that encloses the hoof, will be constructed to prevent or reduce ice from migrating under the hoof. For example, a predetermined amount of neoprene or the like may be used to form a water shoe, or inner slipper, with a non-slip surface underneath the hoof to shield the bottom of the hoof 101 from ice.

In some embodiments, the boot 100 may include status sensors 207. For example, status sensors 207 may include a fluid level indicator, a thermometer, an electronic sensor applied to the horse leg (e.g., to measure skin temperature, pulse rate, etc.), and so forth. The sensor data may be monitored and recorded over time. A processor coupled to a memory and to the status sensor 207 may be provided, either as part of the boot 100, or remotely from the boot 100 but communicatively coupled to the sensor (e.g., a wired or wireless interface). In some embodiments, the processor may be programmed by instruction code stored in the memory to provide a profile of treatment, either on demand or upon a regular schedule (e.g., a daily report). In some embodiments, the processor and communication interface may be configured to allow or provide remote access and/or control by a remote monitoring system or remote supervisory system. In some embodiments, the monitoring system or supervisory system may be configured to show a profile of treatment, e.g., as-provided treatment by itself, or as-provided treatment overlaid with sensor data, etc.

Although some figures include specific dimensions, other embodiments may provide the cryotherapy equine cryotherapy overleg device in different dimensions, including different ratios of dimensions. For example, a larger boot 100 may be provided for larger breeds of mature horses (e.g., a Shire, a Percheron, a Clydesdale, or other draft horse, etc.), and a smaller boot 100 may be provided for smaller breeds of horses (e.g., an Arabian, a pony, a miniature breed, etc.), or for an immature horse of any breed (e.g., foal).

Figure 3:
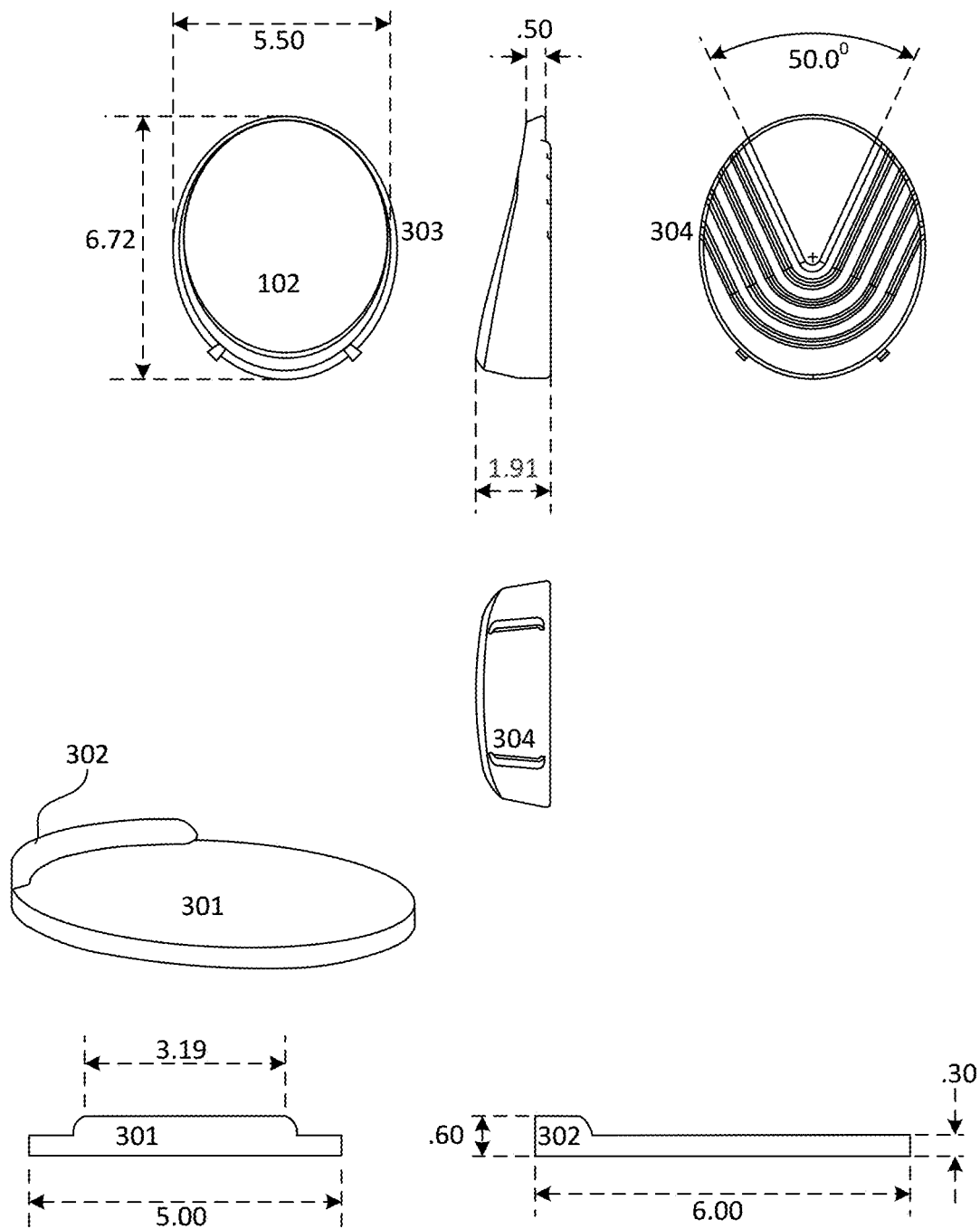
FIG. 3 illustrates various views of exemplary embodiments of a lower portion that may be fitted to a horse's hoof.

Referring now to FIG. 3, various views of exemplary embodiments of a lower portion hoof cover 103 that may be fitted to a horse hoof are illustrated. A bottom portion 301 of the equine cryotherapy boot 100 may include a pliable, durable material that may be secured to the lower portion of the horse leg, such as a hoof wall 302. Securing to the horse may be done with various designs or materials; such as, for example, via hook-and-loop fastener and elastic straps. Lower portion hoof cover 103 may range in a "hoof shaped" circumference 303 of approximately 12 inches for a small equine cryotherapy boot 100, to 20 inches for a large equine cryotherapy boot 100.

An upper portion pastern component 110 101 of the equine cryotherapy boot 100 may be secured to the leg of the horse via an attachment mechanism that generally corresponds to a vertical dimension of the horse leg. By way of non-limiting example, the attachment mechanism may include a zipper 113 fixedly attached to a seam in the upper portion pastern component 110 101. The seam may run along the length of the horse leg, or cover a vertical dimension of the horse leg in another pattern, such as a spiral pattern. The spiral pattern 304 may add strength to the overall fastening of the upper portion pastern component 110 101 of the equine cryotherapy boot 100 to the horse leg. Keep?

Figure 4:
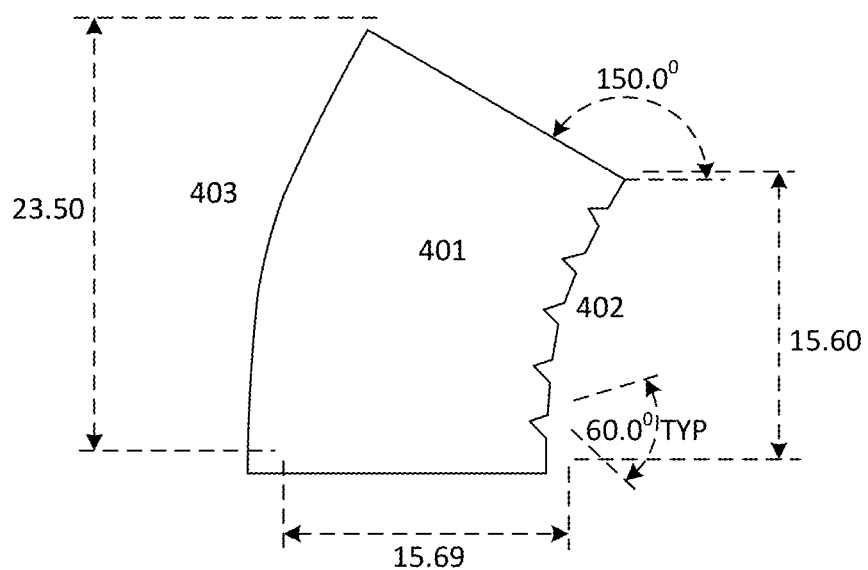
FIG. 4 illustrates an exemplary neoprene shell that may be used in some embodiments of the present invention.

Referring now to FIG. 4, an exemplary flexible shell 401, such as a neoprene shell that may be used in some embodiments of the present invention is shown. The shell may include a side compressed 402 from flexing and a side stretched 403 from flexing.

Figure 5:
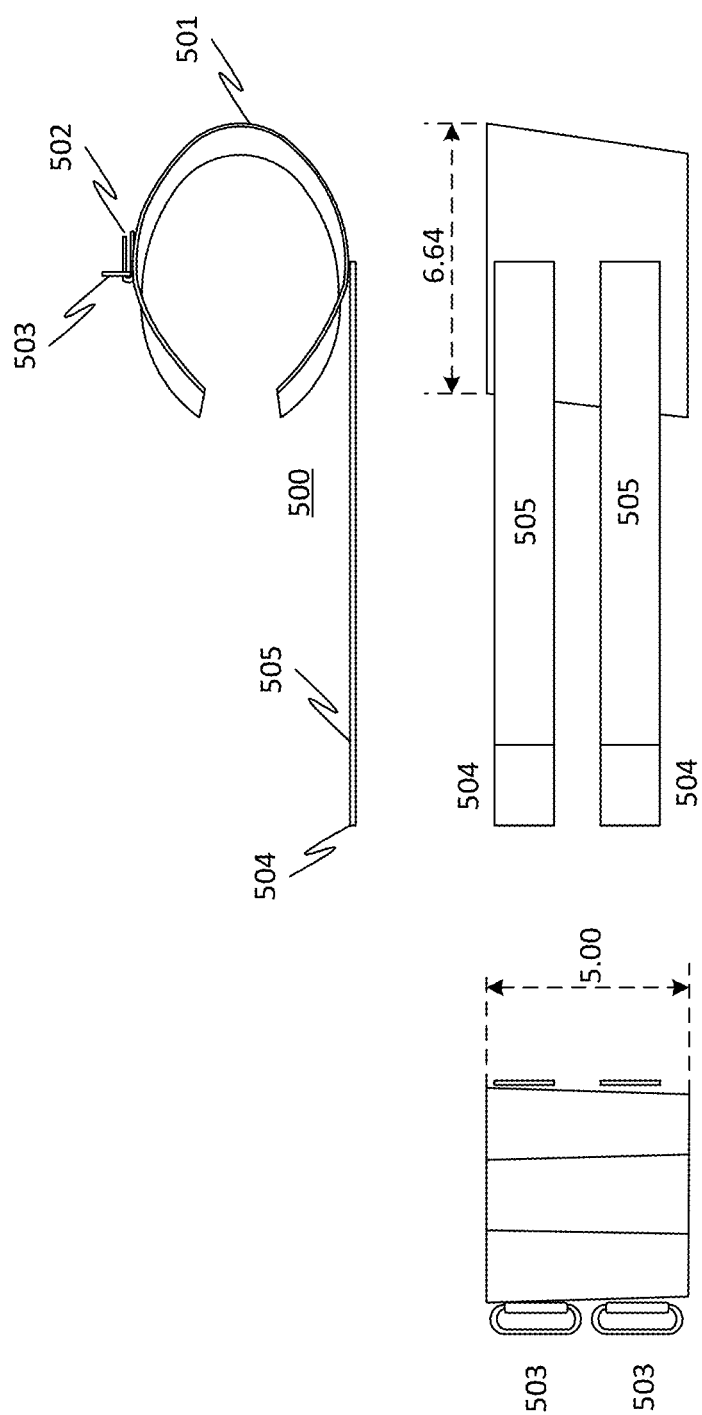
FIG. 5 illustrates an exemplary tether assembly that may be used in some embodiments of the present invention.

Referring now to FIG. 5, an exemplary tether assembly 500 is shown that may be used in some embodiments of the present invention. The tether assembly 500 may include an upper portion 501 with one or more straps 505. The straps 505 may interact with a buckle 503 and/or securing device 502. The straps 505 may also include a securing mechanism 504 on the end of the strap, such as hook and loop (e.g., Velcro), snaps, or hoop and eye.

Figure 6:
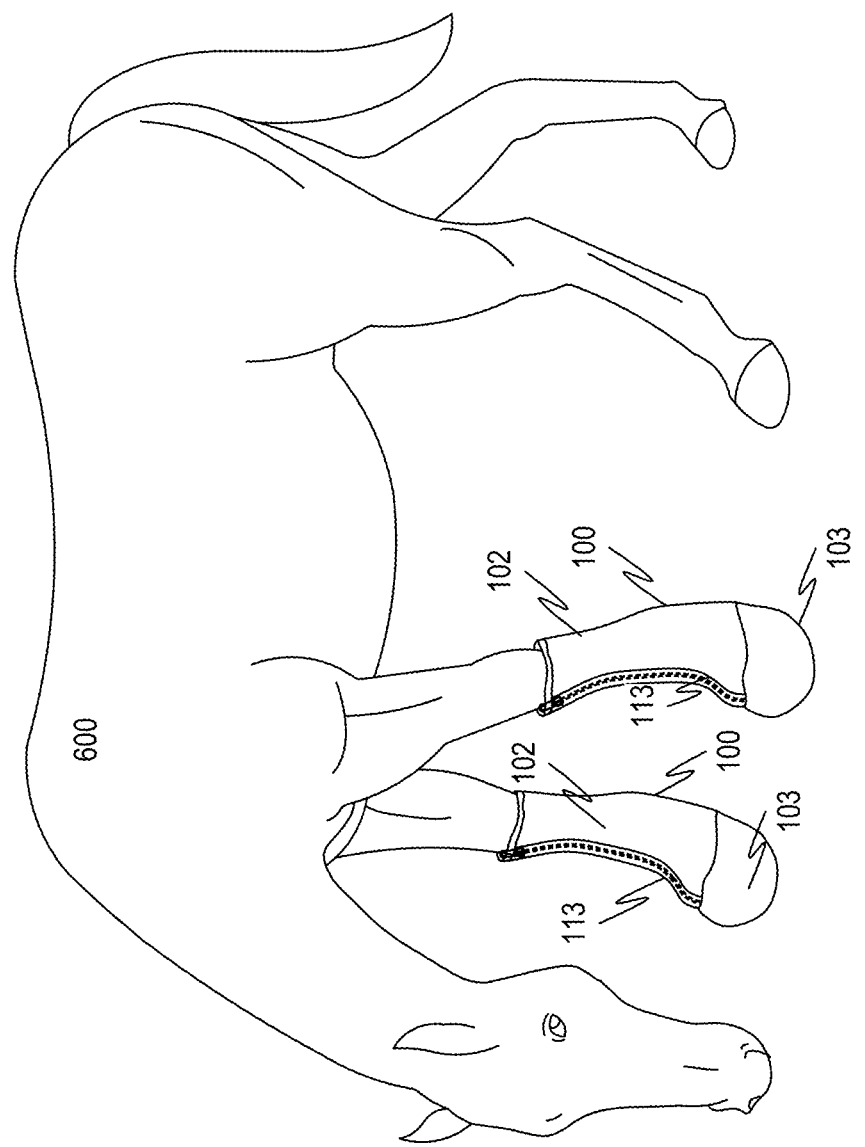
FIGS. 6-6G illustrate aspects of the present invention that correspond with method steps of the present invention.

Referring now to FIG. 6 a cryotherapy boot 100 for administering cryotherapy (or other thermal therapy) to a horse according to the present invention is shown fully installed on a horse 600. As installed, the hoof cover 103 of the cryotherapy boot 100 conceals the horse's hoof and is positioned near the ground as the horse stands. The upper shell 102b conceals ice and the upper compartment tether. A zipper 113 forms a longitudinal seam that may be opened to place ice in the upper compartment and around the upper compartment tether 108.

Figure 6A:
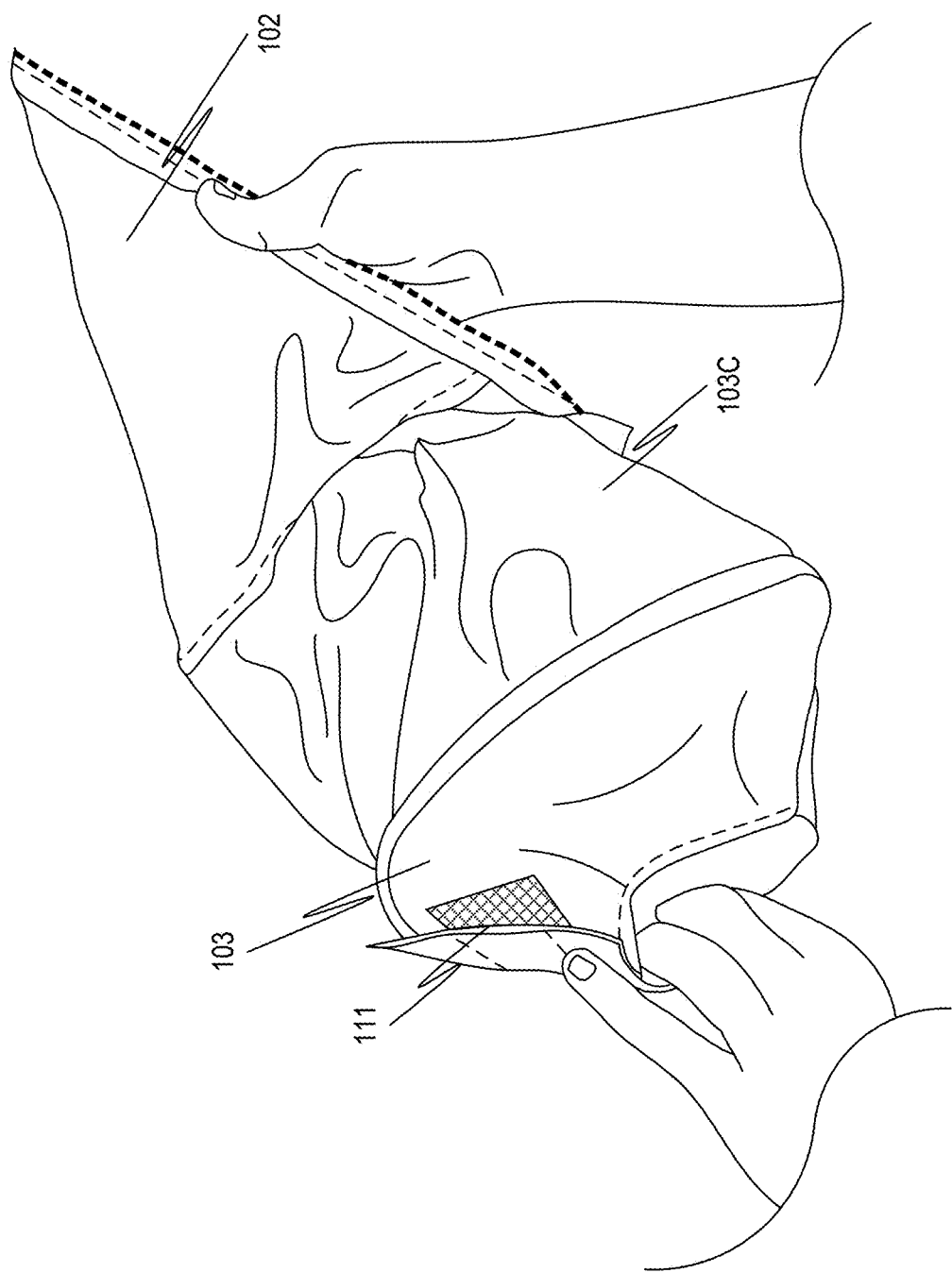

Referring now to FIG. 6A a process for installing a cryotherapy boot 100 on a horse includes turning the boot inside out (as illustrated in FIG. 6A), prior to placing the boot 100 on a horse. Aspects that are viewable with the boot 100 inside out include the hoof cover 103 and a lower shell 103c. The inside out state of the boot 100 extends the lower shell 103c away from the hoof cover 103. While the boot 100 is installed on a horse, the lower shell 103c will encompass the hoof cover 103. A hoof cover fastening device 111 is shown in a fastened position. The method of installing the cryotherapy boot 100 will also include placing the hoof cover fastening device in an unfastened position.

Figure 6B:
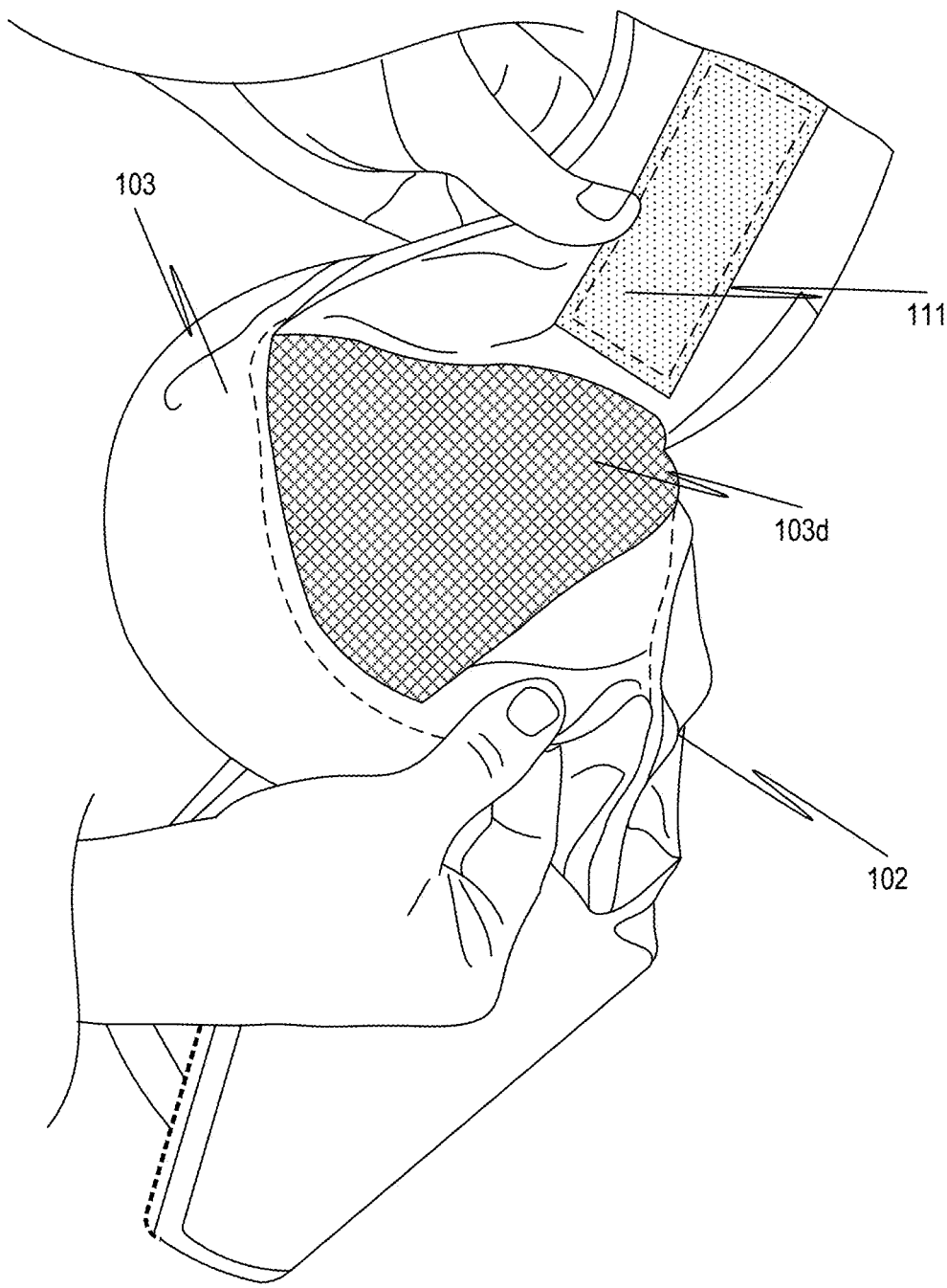
Figure 6C:
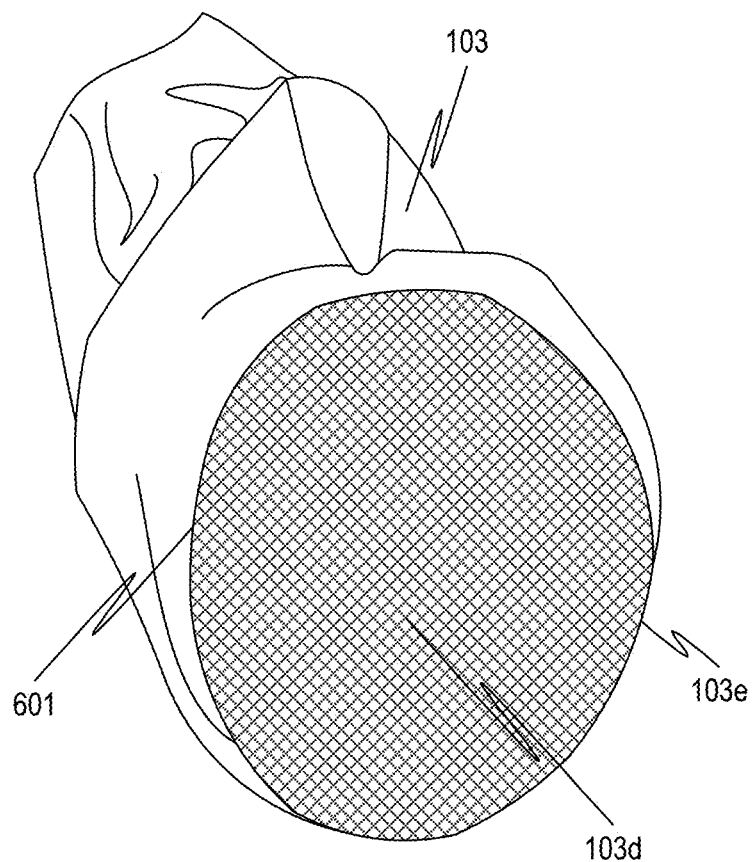

FIG. 6B illustrates the cryotherapy boot 100 in an unfastened state. As illustrated, a hoof cover fastening device 111 may be placed in an unfastened state via the step of unclasping the lower fastening device (also referred to as the hoof securing device 111). FIG. 6C illustrates a hoof cover bottom 103d that may be located a bottom of hoof cover 103 and will generally be formed from rugged material and non-slip material. In some embodiments, a hoof cover bottom 103d may be attached via a hoof bottom seam 103d to the hoof cover 103 which may be located along a perimeter (601) of the hoof cover bottom 103d. The hoof bottom seam 103e may be fixedly attached via stitching, glue, or other fixed attachment means.

Figure 6D:
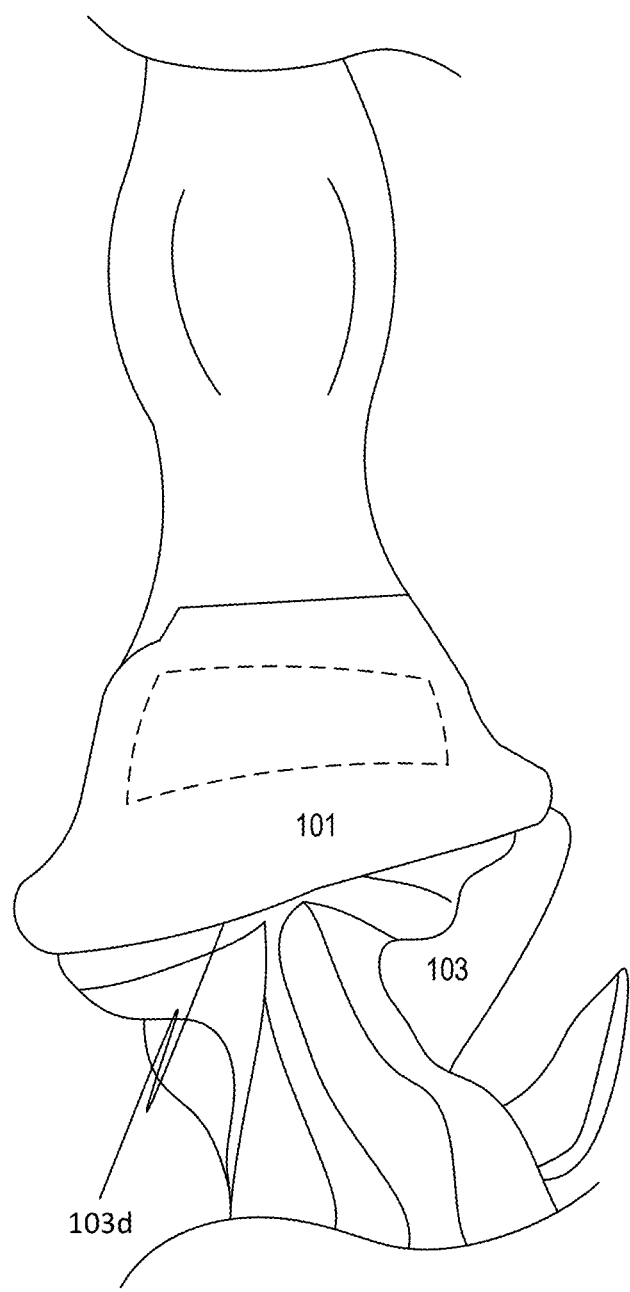

Referring ow to FIG. 6D the method of installing the cryotherapy boot includes placing inside out boot 100 being placed upon the horse's hoof 10. As illustrated, an interior surface (not viewable in 6D) of the hoof cover bottom 103d is placed against a bottom of the horse's hoof 101 and while the hoof cover 103 is inside out and the hoof cover fastener is in an unfastened state.

Figure 6E:
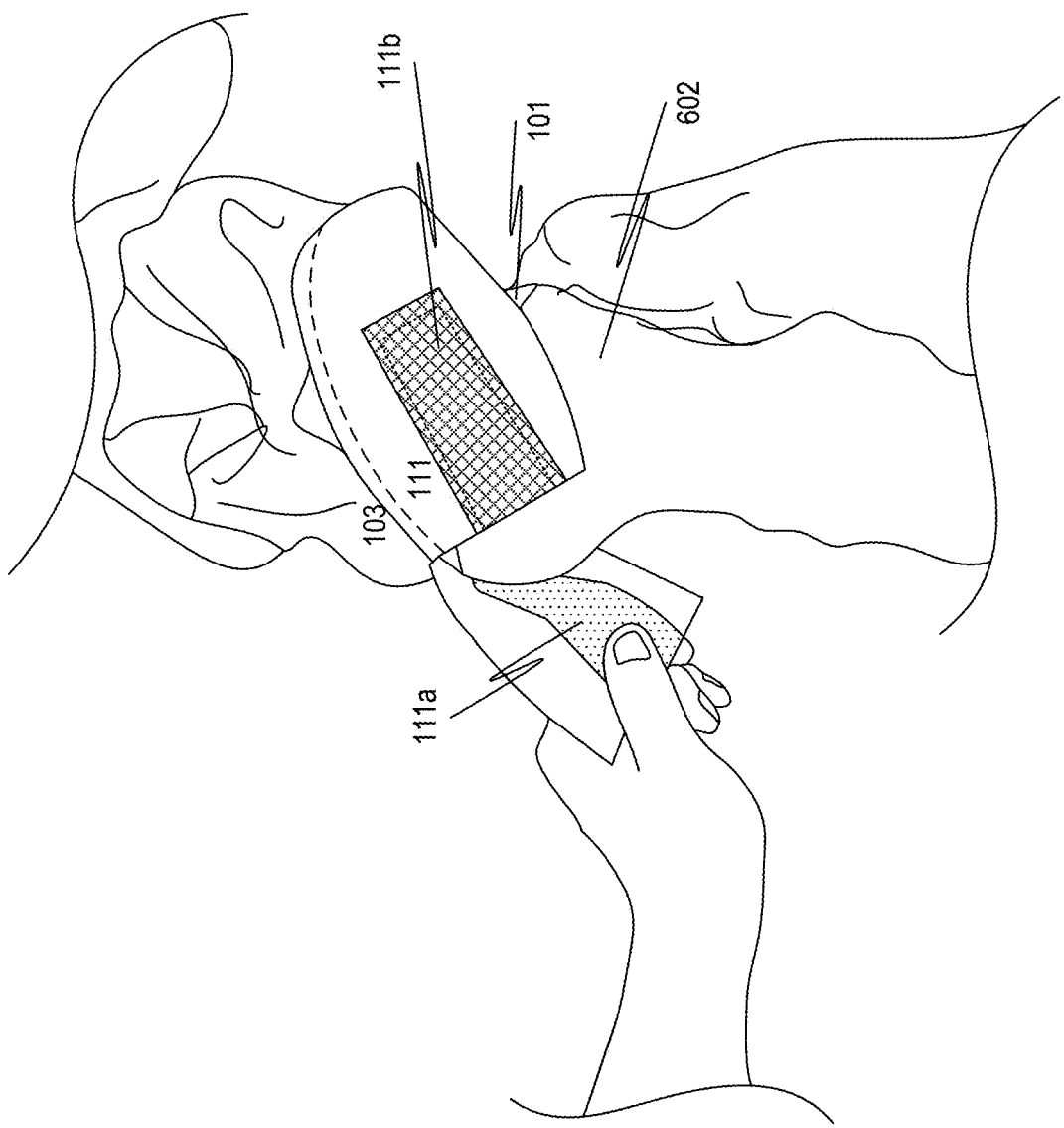

Referring now to FIG. 6E with the boot 100 maintained in an inside out state, and the hoof 101 placed against the interior surface of the hoof cover bottom 103d the method of installing the boot 100 includes pulling the hoof cover 103 over the hoof 101 and aligning a first half 111a of the hoof cover fastening device 111 (sometimes called the lower fastening device) with a second half 111b of the hoof cover fastening device 111. As illustrated, the horse's leg 602 is pulled upward and backward as is typically done to inspect and clean a horse's foot. Positioning the horse's leg 602 and hoof 101 upward and backward can facilitate easy installation of the boot 100 on the hoof 101.

Figure 6F:
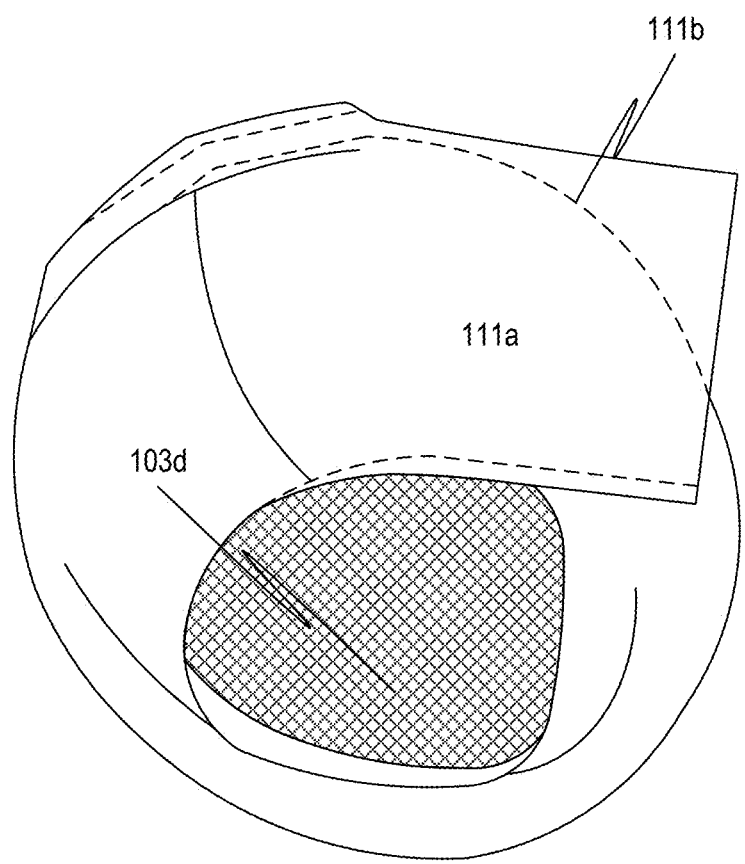

Referring now to FIG. 6F with the hoof cover placed over the hoof of a patient horse, a method may include fastening the hoof cover fastening device 11. Preferably, the boot will be positioned with a hoof cover 103 with a first half 111a of the hoof cover fastening device 111 fastened to a second half 111b of the hoof cover fastening device 1117 boot is illustrated without a horse's hoof contained in the hoof cover.

Figure 6G:
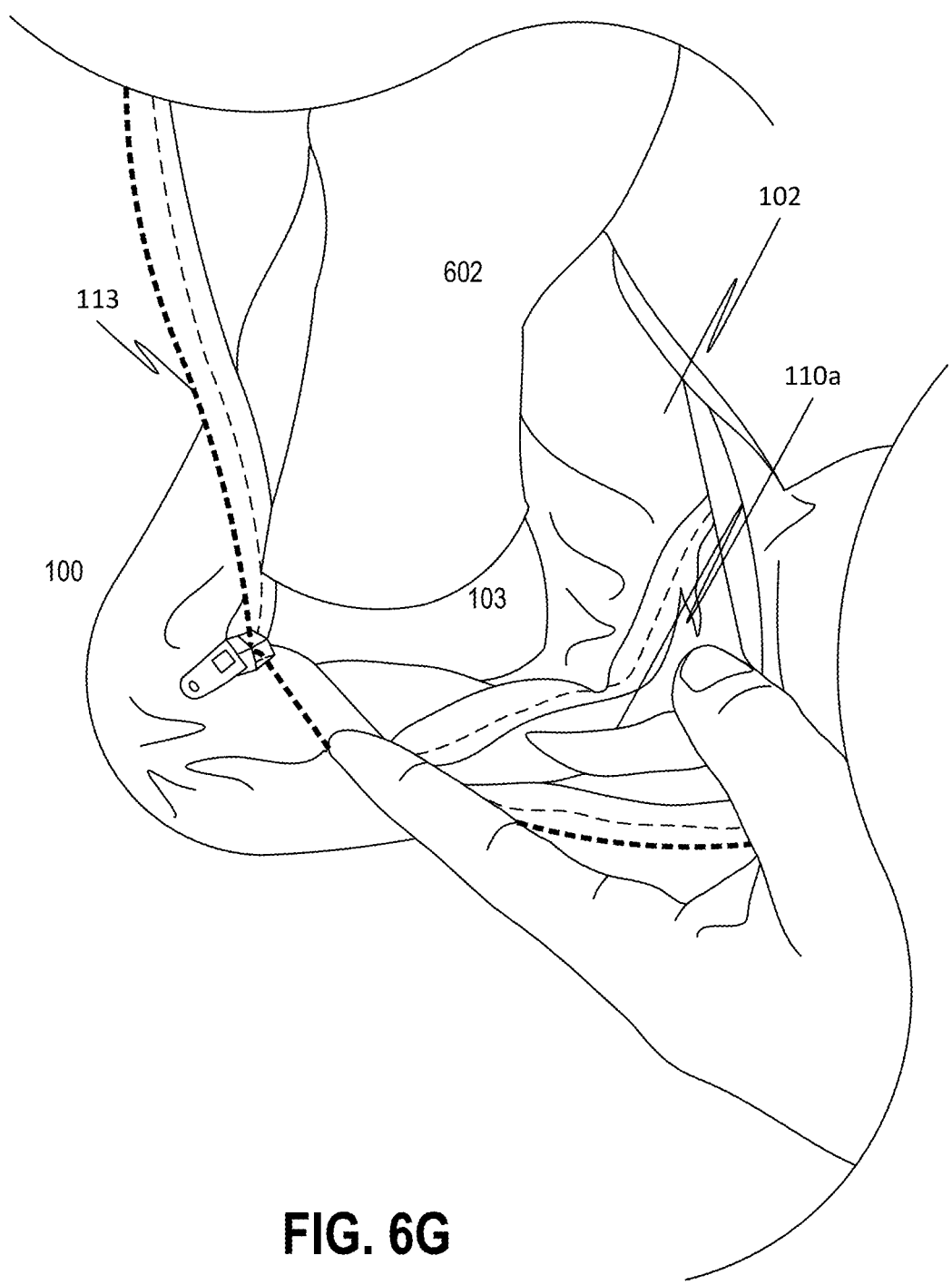

Referring now to FIG. 6G, the process of installing a cryotherapy boot 100 on a horse continues with the horse's leg 602 being returned to normal upright position. The hoof cover fastening device 111 is fastened to place the hoof cover 103 in a state snugly positioned around the horse's hoof (not shown). The state of snugly fit may include, in some embodiments, a state tight enough to limit movement of the boot on the hoof and loose enough to not cause harmful constriction for the horse. The zipper 113 is in an open state and the interior surface of the pastern component 110a of the upper shell 102b is exposed.

Figure 7:
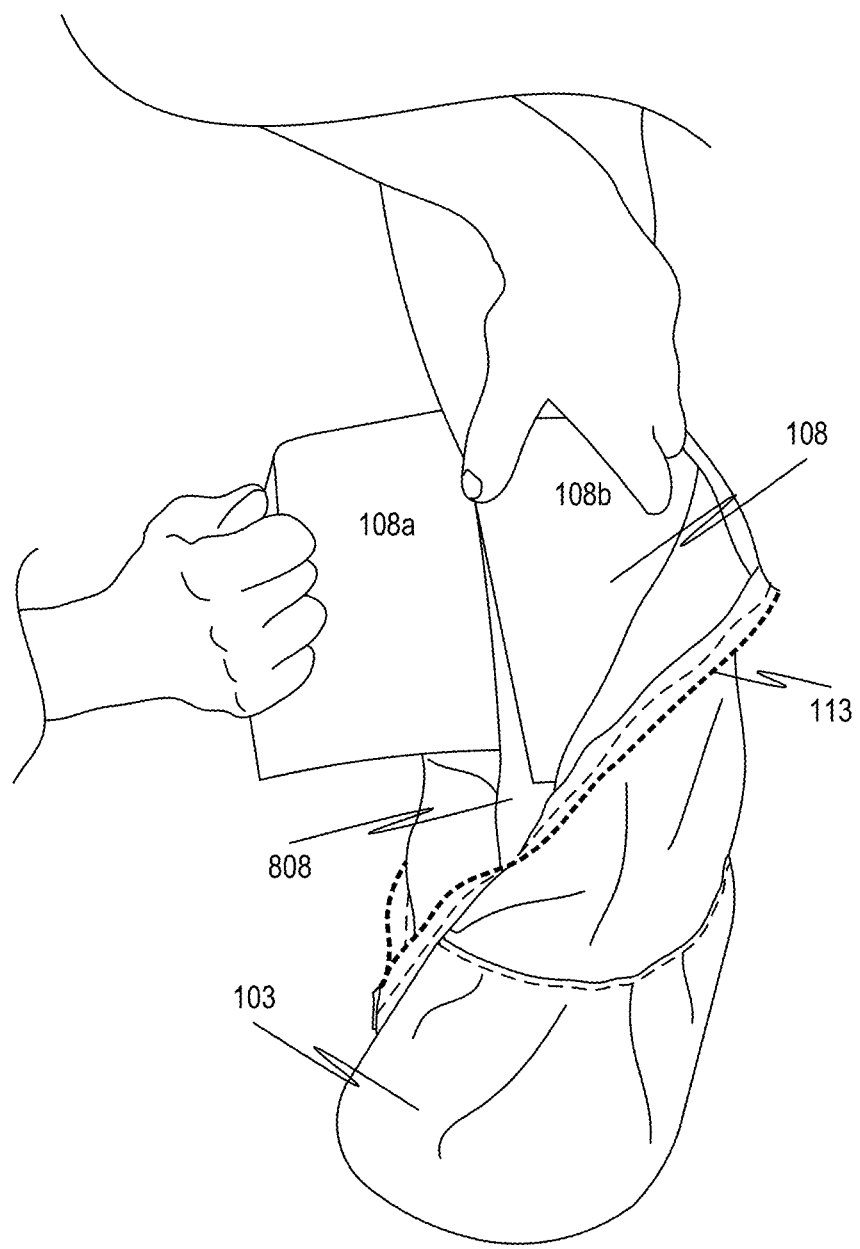
FIGS. 7-7A illustrate additional aspects of the present invention that correspond with additional method steps of the present invention.

Referring now to FIG. 7, a process of installing a cryotherapy boot 100 on a horse may also include the step of fastening the upper compartment tether 108. The upper compartment tether 108 may be fastened by fixing a first tether side 108a with a second tether side 108b. The tether sides 108a-b are preferable fixed via removable fixing devices, such as hook and loop, snaps, buttons buckles and the like. In some embodiments, such as for example a one use disposable embodiment, an adhesive may be used to fix the first tether side 108a to the second tether side 108b. As illustrated, the tether sides are accessible, and fixed, while the zipper is placed in an unzipped state and the horse's hoof is installed in the hoof cover 103. Preferably the hoof cover fastening device is fastened prior to fixing the tether 108 in place.

Preferred embodiments also provide that a pressure of the horse's leg resulting from fixing the tether 108 provides sufficient mechanical support to maintain the boot 100 in position but not so constricting that it adversely restricts circulation or imparts some other adverse physiological symptom to the patient horse.

Figure 7A:
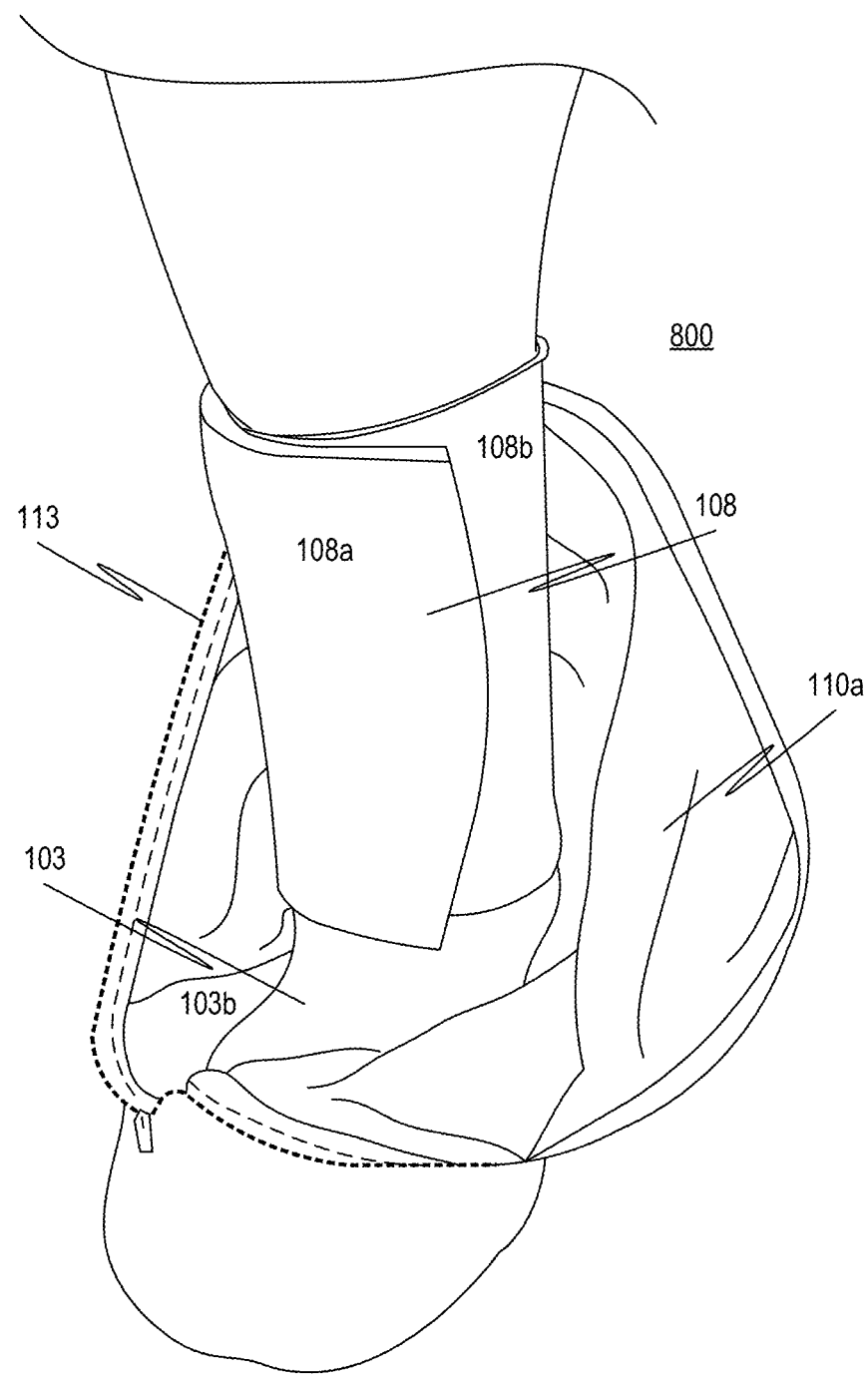

Referring now to FIG. 7A, a cryotherapy boot 100 is illustrated with the tether 108 fastened about the leg of the horse covering a portion of the pastern region 106 and the canon bone region 109, the tether 108 is fastened with a first tether side 108a fixed to a second tether side 108b. A method of installing the cryotherapy boot for administration of cryotherapy treatment includes fastening the upper compartment tether causing the outer shell to be supported in an upright position on the patient horse's leg. The hoof cover is in position covering the hoof and preferably the hoof cover fastening device 111 is fastened. Although it has been presented to fasten the hoof cover fastening device 111 first, it is within the scope of the present invention to fasten the hoof cover fastening device 111 or the tether 108 in any sequential order, or simultaneously.

Figure 8:
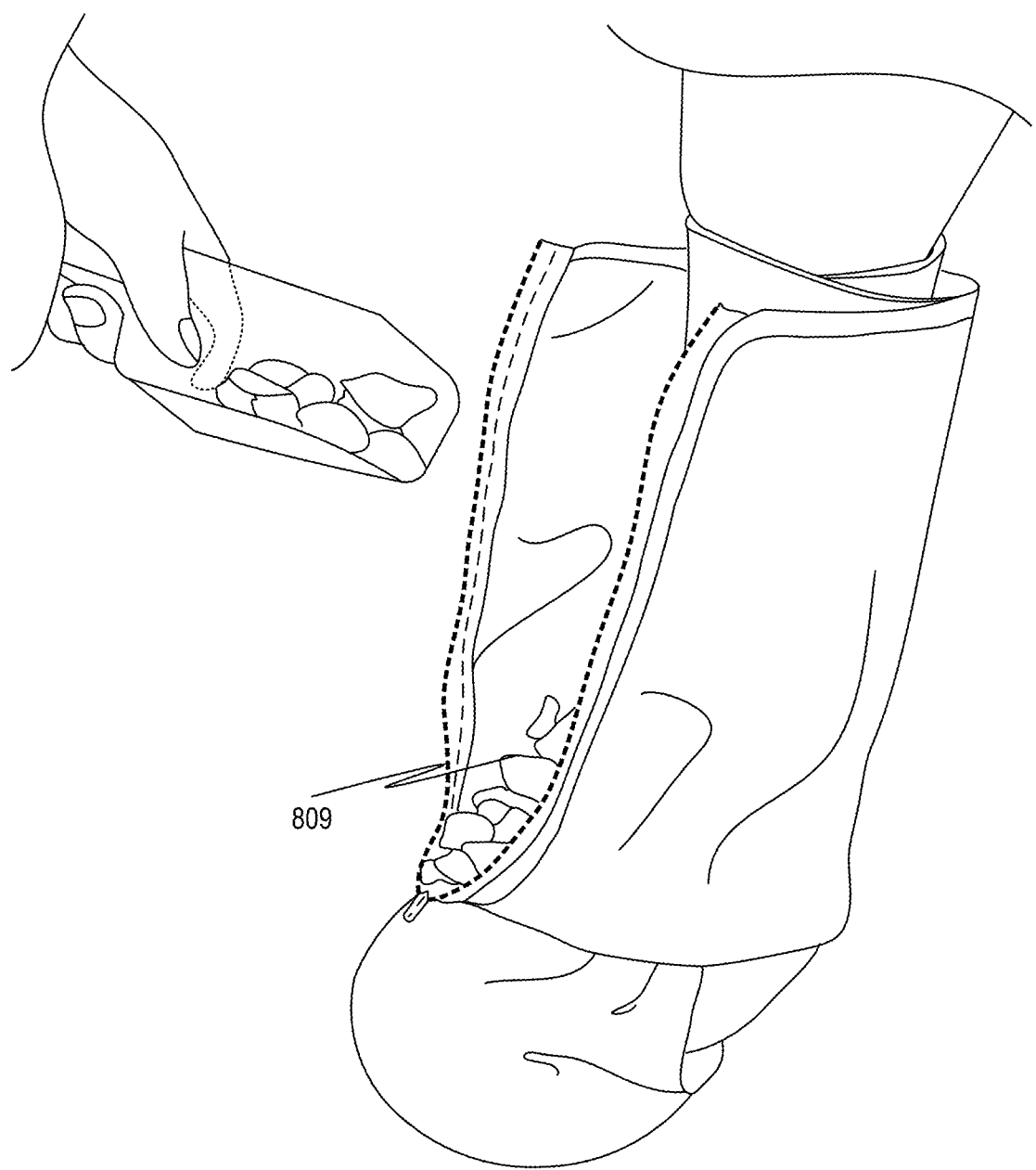
FIGS. 8-8C illustrate still further aspects of the present invention that correspond with additional method steps of the present invention.

Referring now to FIG. 8, with the hoof 101 in the cryotherapy boot 100 and secured by in the lower compartment 103b by the hoof cover 103, and the upper compartment tether 108 secured around the horse's leg 602 thereby supporting the cryotherapy boot 100 in a vertical position encompassing the hoof 101, the middle phalanx 101a, the pastern region 106 and the canon bone region 109 of a horse, the process includes inserting ice (or other thermal component) into the ice containment area 115 included in the upper compartment 102a that is within the upper shell 102b.

Figure 8A:
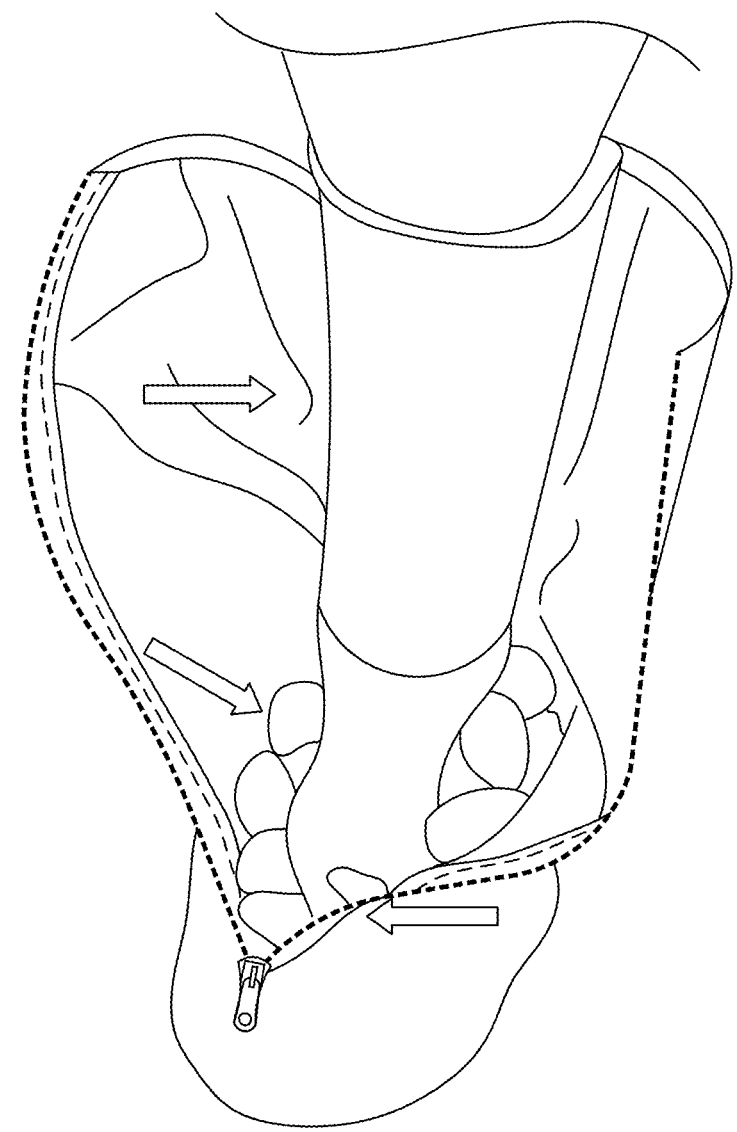

Referring now to FIG. 8A, the processes may include incrementally raising the zipper 113 as a level of ice 104 is also incrementally raised within the ice containment area 115. As such, if a volume of ice 104 is placed into the ice containment area 115 but does to fill the ice containment area 115, the zipper may be raised enough to retain the ice 104 within the ice containment area 115, and also allow access to the upper compartment 102a to insert additional ice 104.

Figure 8B:
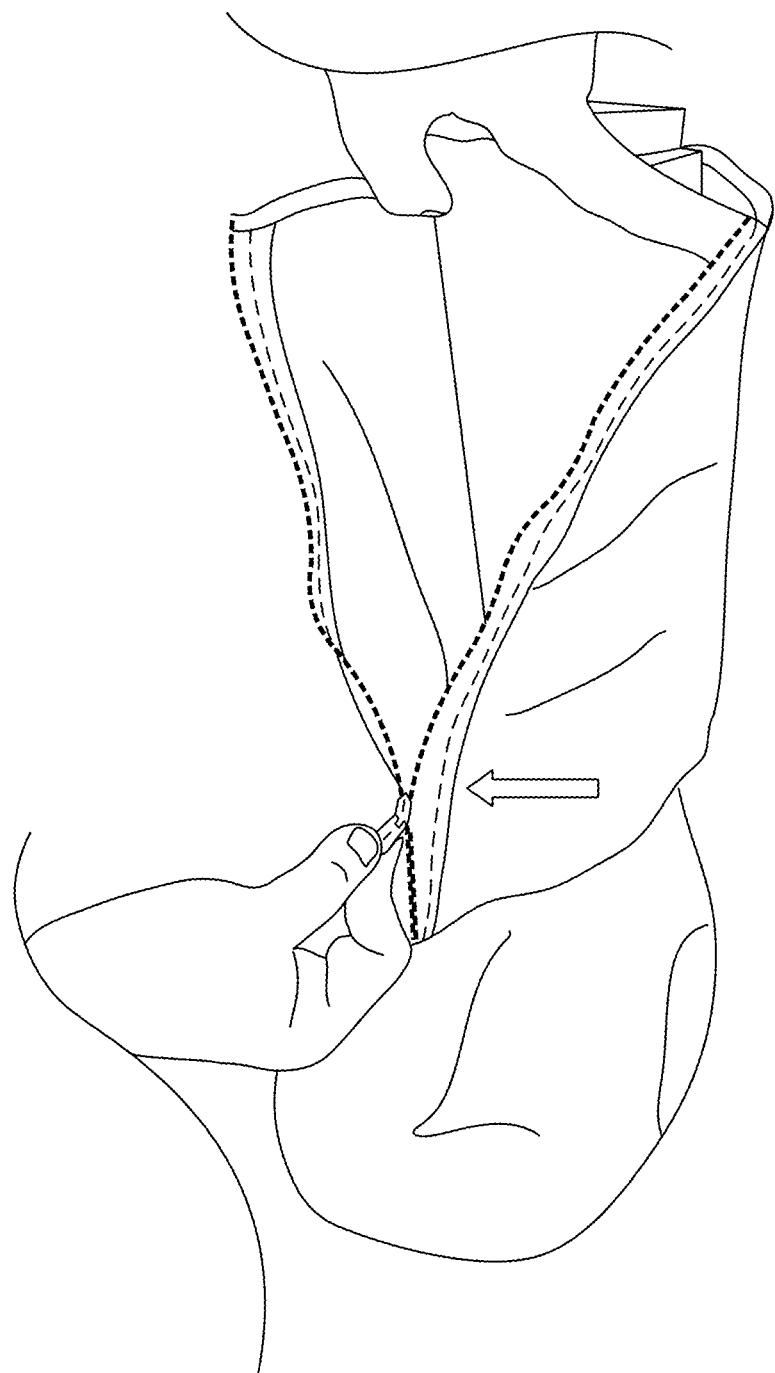

Referring now to FIG. 8B the zipper 113 (or other upper compartment access device 113) may be raised to cause the upper shell 102b to form a contiguous perimeter around the horse's leg and that closes the upper compartment 102a and contain the ice within the ice containment area 115.

Figure 8C:
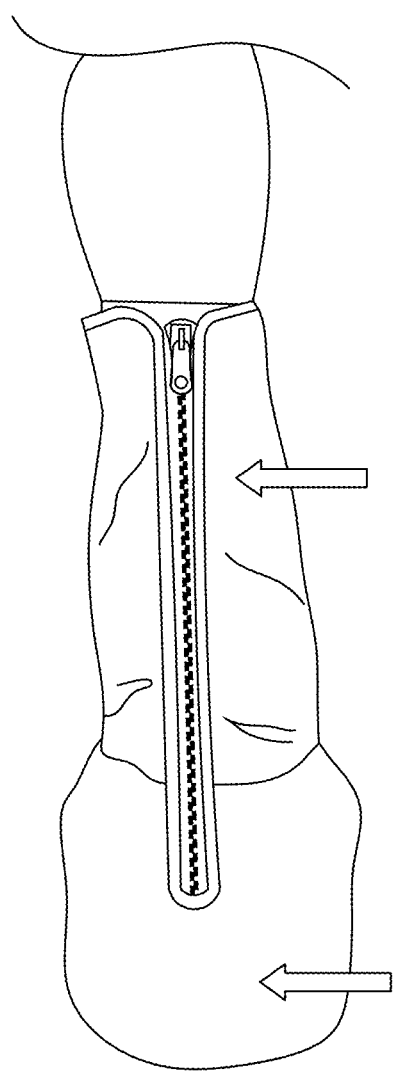

Referring now to FIG. 8C a cryotherapy boot 100 with a fully raised zipper 113 places the boot 100 in a closed state with ice contained within the upper compartment 102a in the ice containment area 115 and the horse's leg 602 free to move about a horse stall without the Cryotherapy boot 100 becoming dislodged. The cryotherapy boot 100 is supported in a vertical position by the upper compartment tether 108 and secured to the hoof 101 by the hoof cover 103 and hoof cover fastening device 111.

Referring now to FIG. 9, method steps 900 for administering cryotherapy to a horse according to some embodiments of the present invention may include, beginning at step 901, turning a cryotherapy boot inside out, said cryotherapy boot comprising a hoof cover, a hoof cover bottom, a hoof fastening device, a lower shell, an upper shell, upper compartment tether, and an upper compartment access device, and at step 902, placing the hoof cover device in an unfastened state;

at step 903, with the cryotherapy boot in an inside out hoof cover device in an unfastened state, placing the hoof cover bottom against a bottom of a hoof of a patient horse;

at step 904, with the cryotherapy boot in an inside outstate state and the hoof cover device in an unfastened state, and the hoof cover bottom against the hoof of the patient horse, pulling the hoof cover over the hoof of the patient horse;

at step 905, fastening the hoof cover fastening device to hold the hoof cover in a state snugly positioned around the hoof;

at step 906, with the hoof cover fastening device in a fastened state and the hoof cover positioned snugly about the hoof of the patient horse; and the upper shell in an open state with the upper compartment access device in an unfastened state, fastening the upper compartment tether thereby causing an outer shell to be supported in an upright position on a patient horse's leg;

at step 907, with the hoof in the cryotherapy boot and secured by in the lower shell by the hoof cover, and the upper compartment tether secured around the patient horse's leg thereby supporting the outer shell in a vertical position on the leg of the patient horse, inserting ice into an ice containment area within the upper shell; and at step 908, raising an upper containment access device to cause the upper shell to form a contiguous perimeter around the leg of the patient horse.

CONCLUSION

A number of embodiments of the present disclosure have been described. While this specification contains many specific implementation details, there should not be construed as limitations on the scope of any disclosures or of what may be claimed, but rather as descriptions of features specific to particular embodiments of the present disclosure.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain embodiments, multitasking and parallel processing may be advantageous. Nevertheless, it will be understood that various modifications may be made without departing from the spirit and scope of the claimed disclosure.

What is claimed is:

1. A method for administering cryotherapy to a horse, the method comprising the steps of:

a) turning a cryotherapy boot inside out, said cryotherapy boot comprising a hoof cover, a hoof cover bottom, a hoof fastening device, a lower shell, an upper shell, upper compartment tether, and an upper compartment access device, and the step of b) placing the hoof cover device in an unfastened state;

c) with the cryotherapy boot in an inside out state and the hoof cover device in an unfastened state, placing the hoof cover bottom against a bottom of a hoof of a patient horse;

d) with the cryotherapy boot in an inside out state and the hoof cover device in an unfastened state, and the hoof cover bottom against the hoof of the patient horse, pulling the hoof cover over the hoof of the patient horse;

e) fastening the hoof cover fastening device to hold the hoof cover in a state snugly positioned around the hoof;

f) with the hoof cover fastening device in a fastened state and the hoof cover positioned snugly about the hoof of the patient horse; and the upper shell in an open state with the upper compartment access device in an unfastened state, fastening the upper compartment tether thereby causing an outer shell to be supported in an upright position on a patient horse's leg;

g) with the hoof in the cryotherapy boot and secured by in the lower shell by the hoof cover, and the upper compartment tether secured around the patient horse's leg thereby supporting the outer shell in a vertical position on the leg of the patient horse, inserting ice into an ice containment area within the upper shell;

h) raising the upper containment access device to cause the upper shell to form a contiguous perimeter around the leg of the patient horse; and i) weeping fluid resulting from melting ice through the upper compartment access device.

2. The method of claim 1 wherein the upper compartment access device comprises a zipper.

3. The method of claim 2, wherein the zipper is at least partially unfastened at step d) in a sufficient amount that an interior surface of a paster component is viewable during step d).

4. The method of claim 3, wherein the zipper is fully closed at step h) and the cryotherapy boot is sufficiently supported in a vertical position by the upper compartment tether, and secured to the hoof by the hoof cover and hoof cover fastening device, to allow the horse to move about a stall without the cryotherapy boot becoming dislodged.

5. The method of claim 4, wherein the step of turning a cryotherapy boot inside out comprises exposing an inner shell of the hoof cover to view.

6. The method of claim 5, wherein the step of turning a cryotherapy boot inside out comprises exposing a hoof slipper to view.

7. The method of claim 4, wherein the hoof cover fastening device comprises a hook and loop fastening device and the method further comprises the step of fastening the hook and loop fastener.

8. The method of claim 4, wherein the upper compartment access device comprises a zipper.

9. The method of claim 8, wherein when the zipper is unfastened at step d) an interior surface of a pastern component is viewable.

10. The method of claim 8, wherein prior to set c) leg of the patient horse is pulled upward and backward to better access the hoof.

11. The method of claim 8, wherein the step of fastening the upper compartment tether comprises fixing a first tether side to a second tether side.

12. The method of claim 11, the first tether side comprises a hook fastener and the second tether side comprises a loop fastener.

13. The method of claim 12, wherein the step of fastening the upper compartment tether by fixing a first tether side to a second tether side comprises sufficient mechanical support to maintain the boot in an upright position but not so constricting that it adversely restricts circulation or imparts some other adverse physiological symptom to the horse patient.

14. The method of claim 12, wherein the tether is fastened about the leg of the patient horse covers a portion of a pastern region and a canon bone region of the patient horse.

15. The method of claim 14, wherein the tether is fastened about the leg of the patient horse causes the outer shell to be supported in an upright position on the patient horse's leg.

16. The method of claim 14, wherein with the hoof of the patient horse in the cryotherapy boot and secured by hoof cover fastener, and the upper compartment fastening device secured around the horse's leg, the method further comprise the step of supporting the outer shell in a vertical position so that the cryotherapy boot encompasses the hoof, a middle phalanx, a pastern region and a canon bone region of the patient horse.

17. The method of claim 11, additionally comprising the steps of incrementally raising the zipper as a level of ice placed in the cryotherapy boot is incrementally raised.

18. The method of claim 11, wherein, if a volume of ice placed within the Cryotherapy boot does to fill an ice containment area, the zipper may be raised enough to retain the ice within the ice containment area, and also allow access to the upper compartment to insert additional ice into the ice containment area.

19. The method of claim 18, additionally comprising the step of supporting the cryotherapy boot in a vertical position via the upper compartment tether and securing the cryotherapy boot to the hoof of the patient horse via the hoof cover and hoof cover fastening device; and weeping fluid through one or both of the zipper and a weep portal.

* * * * *